United States Patent
Murphy

(10) Patent No.: US 6,576,672 B1
(45) Date of Patent: *Jun. 10, 2003

(54) POLYAMINE TREATMENT OF NEUROLOGICAL DISORDERS

(76) Inventor: Michael A. Murphy, 5619 Chelsea Ave., La Jolla, CA (US) 92037

(*) Notice: Subject to any disclaimer, the term of this patent is extended or adjusted under 35 U.S.C. 154(b) by 0 days.

This patent is subject to a terminal disclaimer.

(21) Appl. No.: 09/486,310
(22) PCT Filed: Aug. 21, 1998
(86) PCT No.: PCT/US98/17301
§ 371 (c)(1), (2), (4) Date: Feb. 23, 2000
(87) PCT Pub. No.: WO99/08519
PCT Pub. Date: Feb. 25, 1999
(51) Int. Cl.[7] .................. A61P 25/28; A61K 31/131; A61K 31/395; A61K 31/4965; A61K 31/785
(52) U.S. Cl. .................. 514/674; 514/183; 514/255; 424/78.17
(58) Field of Search .................. 514/674, 654, 514/655, 255, 183; 424/422

Primary Examiner—Edward J. Webman
Assistant Examiner—Helen Nguyen
(74) Attorney, Agent, or Firm—Henri J. A. Charmasson; John D. Buchaca

(57) ABSTRACT

2,3,2 Tetramine (3,7-diazanonane-1,9-diamine) is propounded for treatment of Parkingson's Disease and dementias characterized by mitochondrial damage in view of this compound's ability to completely neutralize the dopamine-depriving effect of MPTP in laboratory animals up to 12 hours post MPTP injection, and to retain partial protection at suboptimal tissue levels for up to 36 hours. The effect of injecting combinations of MPTP and/or reducing agents and/or xenobiotics and/or depigmenting agents on Dopamine, Norepinephrine, Serotonin and Epinephrine levels demonstrated that MPTP and MPP+ act as reducing agents that mobilize copper and calcium, and sequester iron, and that the vulnerability of dopamine to these types of neurotoxins and to xenobiotics and metals can be corrected by administration of 2,3,2 tetramine that appears to redistribute metals between diverse storage pools and free metals in cytosol and regulate receptor mediated events, among other antidotal effects analogous to those of some of the endogenous polyamines.

14 Claims, 7 Drawing Sheets

Mean Brain Dopamine concentration in uM versus Time in hours

Mean Brain Dopamine concentrations of all groups

Brain Norepinephrine Percentage of Control Values versus Time Following PBN and or TEMPO and or MPTP Administration Serotonin Percentage of Control Values versus Time Following PBN and or TEMPO and or MPTP Administration

POLYAMINE TREATMENT OF NEUROLOGICAL DISORDERS

FIELD OF THE INVENTION

This invention relates to the treatment of neurological disorders in mammalian subjects, and more specifically to the diagnosis and therapy of Parkinson's Disease, Olivopontine Cerebellar Atrophy, Alzheimer's Disease and Lou Gehrig's Disease.

BACKGROUND OF THE INVENTION

Parkinson's Disease is a degenerative disease of the nervous system which affects one person in fifty over fifty years of age and one person in twenty over seventy years of age, without gender or social bias. Described by James Parkinson in 1817, the shaking palsy is comprised of a triad of tremor at rest, muscular rigidity and slowness of movement. Accurate description of the disease during the period of the Industrial Revolution has prompted people to speculate that environmental exposure to toxic chemicals precipitates the disease. Exposure to manganese precipitated a Parkinsonian syndrome in miners which also includes schizophreniform behaviors. Some epidemiologic studies have found association between industrial exposure to copper, manganese and copper simultaneously with iron and the incidence of Parkinson's disease (Gorell J. M et al), between incidence of Parkinson's disease and blood mercury levels (Ngim C. H. et al) and with death rates from Parkinson's Disease and proximity to iron and copper related industrial processes (Rybicki B. A. et al). Xenobiotics, natural and man made insecticides have also been suggested as candidate agents because they precipitate on occasion motor disturbances in animals and man somewhat akin to Parkinsonism. Thus both inorganic and organic chemicals may contribute to the toxicity mechanism. Other types of Parkinsonism include post encephalitic, Wilson's Disease and Parkinsonism secondary to cerebrovascular accidents, space occupying lesions and drug induced. The disease is progressive though not in all cases. Dementia with Alzheimer type pathological changes follows but does not precede the development of Parkinson's Disease in about one quarter of diagnosed cases.

Generalized wasting and anorexia also occur, metabolic components of the disease not attributable to hypothalamic (tuberoinfundibular) dopaminergic dysfunction.

PROGRESSION

Parkinson's Disease progresses to differing extents in different patients, most commonly over a seven to ten year timeframe from the time of diagnosis. Some patients experience generalized wasting and anorexia, depression and mental changes frequently occur and approximately one quarter develop Alzheimer type clinical changes in cognitive functioning and measurable Alzheimer pathological changes in up to forty percent of cases.

PHENOMENOLOGY

A. Iron Deposition and Copper Displacement

Iron is deposited as haemosiderin granules in the cytoplasm, and mitochondria filled with ferritin granules have been observed in the neuronal and glial cells of the ventrolateral thalamus, caudate and lenticular nuclei and substantia nigra of Parkinsonian brains (Earle K. M., Asenjo A. et. al., Riederer P. et. al.), and copper, though not detectable in excess in the brain, does overflow into the cerebrospinal fluid. The level of copper overflow correlates with the clinical severity of Parkinson's Disease and the level of Alzheimer type damage present in the patients (Pall H. S. et al).

Though Parkinsonian syndromes can be induced by other metals such as chronic manganese poisoning which causes Parkinsonian like and psychotic symptoms in miners and hepatolenticular degeneration due to copper deposition in Wilson's Disease, excessive levels of metals other than iron have not been observed in idiopathic or post encephalitic Parkinsonism.

B. Mitochondrial Morphology

Mitochondria are morphologically distorted and iron is deposited in large quantities, without evidence of deposition of other metals (Earle K. M., Asenjo A. et. al., Riederer P. et. al). Iron and copper may be released from neuromelanin and from damaged mitochondria. Elevated free iron in mitochondria and cytosol and apparent overflow of copper from a storage site through cytosol to cerebrospinal fluid occurs. Inhibition of complex 1 of the mitochondrial electron transport chain depressing mitochondrial respiration occurs in Parkinson's Disease.

C. Thiol Methyltransferase

Thiol methyltransferase activity is reduced in Parkinson's disease and increased in motor neurone disease (Waring et al 1989). Glutathione S transferase activity is present in oligodendrocytes, astrocyte end feet, choroid plexus and ependymal cells. Neither isoform of the enzyme is present in neurons. The enzyme activity is present in white and gray matter oligodendrocytes as the yp form. The yb form is present in astrocytes, ependymal cells and tanycytes. The distribution of the enzyme suggests that it is a first line of defence against toxic substances (Cammer W. et al 1989).

D. Copper Zinc Superoxide Dismutase

High levels of CuZn SOD were demonstrated immunohistochemically in the large pyramidal cells of control and Alzheimer's disease patients brains (Delacourte A. et al 1988). The localization of the superoxide dismutase gene on chromosome twenty one and the early occurrence of Alzheimer's Disease in Down's syndrome suggest that superoxide dismutase activity and hydrogen peroxide formation may contribute to Alzheimer's pathogenesis. Also the neurons containing high levels of NADPH diaphorase are relatively spared in neonatal hypoxia and hypoglycemia but are affected in Alzheimer's disease. The increase in platelet membrane fluidity, noted in a subgroup of Alzheimer's disease patients, possibly due to dysregulation of platelet membrane biosynthesis is not associated with a higher erythrocyte level of superoxide dismutase (Zubenko G. S. et al 1989).

E. Monoamine Oxidase and NADPH Diaphorase

The capacity to produce Parkinsonian damage is correlated with the level of melanization of the substantia nigra of the species, and the activities of monoamine oxidase B and NADPH diaphorase in the basal ganglia.

Monoamine Oxidase

Astrogliosis associated with aging leads to increased MAO B activity and increased susceptibility to the toxin MPTP as do differences in MAO B activity between various mouse strains (Zimmer J. et al 1987). MAO B increases with age in humans and MAO A activity does not (Oreland L. et al 1986). MAO B activity increases more in white matter than in grey matter. MAO B is increased in Alzheimer's disease patients compared with age matched controls, more so in white matter than in gray matter, a thirty two percent per decade increase compared to a twelve percent increase. Monoamine oxidase activity in the brains of alcoholics who committed suicide was lower than that in brains of non alcoholic suicides and controls (Gottfries C. G. et al 1975).

Nicotinamide Adenine Dinucleotide Phosphate Diaphorase

In human brain NADPH diaphorase activity was greater in gray matter than in white matter, and likewise for malic dehydrogenase, succinic dehydrogenase and cytochrome oxidase. In monkey brain NADPH diaphorase has greater activity in nuclei containing much neuropil than in nuclei which were predominantly perikaryal and with lesser activity again in white matter (Friede R. L. et al 1963b). A similar pattern of distribution for NADPH diaphorase, succinic dehydrogenase and cytochrome oxidase was observed in random sections of human brain (Friede R. L. et al 1962).

In the human brainstem NADPH diaphorase containing neurones are located in the vicinity of melanin containing neurones such as the dorsal motor nucleus of the vagus, locus coeruleus and substantia nigra, suggesting a role in the processing of melanin and lipofuscin (Kowall N. W. et al 1988, Friede R. L. et al 1962).

Formation of lipofuscin is correlated with oxidative enzyme activity, but it is readily removed from the neuropil by glial cells whereas it accumulates in perikarya (Friede R. L. 1961). In Alzheimer's disease a subset of non pyramidal neurones, in layers II and III, V and VI of the cerebral cortex and subcortical white matter containing somatostatin, neuropeptide Y and high NADPH diaphorase activity are vulnerable to damage (Kowall N. W. et al 1988). Immunohistochemically somatostatin, neuropeptide Y were present in abnormal neurites whilst perikarya appeared normal. By contrast NADPH diaphorase neurones are resistant to damage in neonatal hypoxia—ischaemia. They appear resistant to excitotoxic damage mediated by the NMDA receptor. Medium sized aspiny neurones which are NADPH diaphorase positive and also stain for neuropeptide Y and somatostatin are preserved in Huntington's disease (Ferrante R. J. 1987). Neuronal NADPH diaphorase activity is reduced in Alzheimer's disease brain, with reduced neuropil staining, suggestive of retrograde degeneration. Glial NADPH diaphorase activity in Alzheimer's disease is increased (Jacobs R. W. et al 1985).

F. Metalloendopeptidases which could cause excessive amyloid production, neurofibrillary tangle formation and tissue damage in dementias.

Pre Aspartate Proteases

Pre aspartate sites are not common sites for cleavage of precursor or prosequences or as degradative sites of proteins of known sequence. They are potentially very interesting in view of the commencement of several proteins and peptides involved in Alzheimer's Disease, hereditary cerebral hemorrhage with amyloidosis—Dutch type, vascular malformations in brain and spinal cord, Batten's Disease, neuronal ageing and high density lipoprotein fractions with aspartate residues.

Rat brain apparently lacks an enzyme of endopeptidase type which cleaves methionine aspartate bonds because cholecystokinin 8 and cholecystokinin 5 peptide hydrolysis indicate the absence of such an endopeptidase. Gly Trp Met formation occurs at thirty times the rate with CCK 5 as substrate as compared with CCK 8 as substrate, and the N terminal pentapeptide which would result from cleavage of the methionine aspartate bond in CCK 8 is not formed (Rose C et al 1988, 1989). Amyloid plaques are not observed in rat brain and the absence of the relevant enzymatic activity may account for this difference.

Interleukin 1 Beta Processing

Interleukin 1 Beta is activated by cleavage at a pre aspartate site by a calcium or magnesium and zinc dependent enzyme (Black R. et al 1989). Interleukin 1 Beta injected into rat brain stimulates astrogliosis and neovascularization (Giulian D. et al 1989). Microangiopathy involving non fenestrated blood vessels is postulated in Alzheimer's Disease (Scheibel A. B. et al 1989). Interleukin 1 Beta stimulates transcription of alpha antichymotrypsin mRNA which latter protein is deposited in amyloid plaques (Baumann H. et al 1987). Alpha 1 antichymotrypsin though not immunohistochemically observable in fetal human brain is observable in adult human brain grey and white matter, choroid and ependymal cells (Justice D. L. 1987). Astrocytes may produce interleukin 1 Beta in the central nervous system. IL-1 Beta level is increased in the cerebrospinal fluid in Alzheimer's Disease (Cacabelos R. et al 1991).

ATPase Subunit 9 Processing

In Batten's Disease amyloid Beta peptide immunoreactivity has been demonstrated (Wisniewski K. E. et al 1989) and a mitochondrial ATPase subunit 9 protein commencing with an aspartate residue is also deposited (Palmer D. N. et al 1989). The processing peptidase is also a metalloendopeptidase (Schmidt B. et al 1984).

Apolipoprotein A1 Processing

Apolipoprotein A1 protein has a hexapeptide pro sequence in addition to its pre sequence. The pro sequence is cleaved at a pre aspartate site by an extracellular metalloendopeptidase (Edelstein C. et al 1983, Kooistra T. et al 1984, Scanu A. M. et al 1987, Edelstein C. et al 1987). An identical hexapeptide in the same position occurs in the apolipoprotein C111 protein but it is not cleaved by the metalloendopeptidase. Genetic linkage has been observed between an apolipoprotein C111 allele and Alzheimer's disease (Schellenberg G. D. et al 1987).

Beta Amyloid Producing

Beta amyloid deposited in Alzheimer's Disease and Hereditary cerebral hemorrhage with amyloidosis—Dutch type has an aspartate amino terminus, (Prelli F. et al 1988), and the Beta amyloid of vascular malformations in brain and spinal cord presumably also has an aspartate amino terminus (Hart M. et al 1988). A calcium dependent serine protease which cleaves at the methionine aspartate site and is inhibited by 1, 10 phenanthroline, EGTA and DFP, alpha 1 antichymotrypsin and secreted beta precursor protein was identified in Alzheimer's disease brain tissue (Abraham C. R. et al 1991a). A metal dependent thiol protease which requires a reducing agent was also partially purified (Abraham C. R. et al 1991b).

The class of enzyme which cleaves the Beta precursor protein at the physiological cleavage site within the Beta peptide sequence as demonstrated by (Sisodia S. S. et al 1989) is not yet known.

Protein C is a cysteine protease which causes Factor Va, Factor VIII inactivation and fibrinolysis and thus has anticoagulant effect. Assuming that cystatin C is a physiological inhibitor of Protein C, then the Cystatin C variant protein in serum and cerebrospinal fluid of Icelandic Hereditary Cerebral Hemorrhage patients cause hemorrhage(s) due to lack of inhibition of Protein C mediated anticoagulation and fibrinolysis. The topographical distribution of this protease and its inhibitor in relation to the sites of hemorrhage in Icelandic Hereditary Cerebral Hemorrhage is not known. The regulation of Factor V levels is further complicated by its requirement for thiol protease, which proteases will also be influenced by thiol protease inhibitors (Rodgers G. M. et al 1987). A metal dependent thiol protease cleaves the methionine aspartate bond of amyloid precursor protein (Abraham C. R. et al 1991).

Bacterial Preaspartate Protease

Pre aspartate proteases exist early in evolution, a zinc and cobalt dependent pre aspartate protease being described in Pseudomonas Fragi (Noreau J. et al 1979). The distribution of pre aspartate proteases in central nervous system and vasculature is not yet described.

Brain Cathepsin D Processing

Mature bovine brain Cathepsin D has an amino terminal aspartate residue (Whitaker J. N. et al 1979), whereas bovine spleen cathepsin D commences with a glycine residue (Press E. M. et al 1960).

Cathepsin D is an aspartyl protease which cleaves the leucine phenylalanine bond of beta endorphin, the alanine alanine bonds of lipotrophin and the phenylalanine phenylalanine bond of myelin basic protein, substance P and somatostatin. Cathepsin D increased in activity in rabbit cortex, hippocampus and spinal cord injected with aluminum (Suzuki H. et al 1988). Alcohol administration to rats at various ages significantly increased cathepsin B and D activities (Suleiman S. A. 1987). Cathepsin D activity increases continually during fetal development (Dorn A. et al 1986). (Matus A. et al 1987) observed a two fold increased activity of cathepsin D like protease in elderly rat brain with increased degradation of MAP 1 and MAP 2 which could cause defective microtubule assembly in Alzheimer's Disease brain as suggested by (Iqbal K. et al 1986).

Other Endopeptidases

Substance P Producing

An endopeptidase generating substance P (1-7) and Substance P (1-8) is a metalloenzyme with essential SH groups which cleaves Phe—Phe and Phe—Gly bonds and is inhibited in a dose dependent manner by calcitonin gene related peptide in non myelinated afferent C fibers in the spinal cord (Nyberg F. et al 1988).

Myelin Basic Protein Endopeptidase

A zinc dependent myelin basic protein degrading endopeptidase distinct from calpains which degrade myelin basic protein in rodents was isolated (Chantry A. et al 1988, Earl C. et al 1988, Groome N. et al 1988). Its distribution in brain is not yet known.

Calcium Activated Neutral Proteases I and II

The level of calcium activated neutral protease activity in white matter corpus callosum is seven times that of grey matter cerebral cortex (Chakrabasti A. K. et al 1989). It is further enriched in myelin fractions which contain fifty percent of the white matter calcium associated neutral protease activity. Likewise calcium associated neutral protease activity is very evident in myelin. Banik N. L. et al 1987 observed that calcium mediated proteolytic activity in white matter degraded proteolipid protein, myelin basic protein and neurofilament triplet proteins in rabbit, rat and bovine brains, and observed lower levels of activity in grey matter than in white matter. Calpain also causes breakdown of neurofilament proteins in ischaemia (Ogata N. et al 1989). Immunohistochemically CANP1 activity is present in neuronal perikarya, axonal and dendritic processes, within spine heads and necks and in glial cells (Perlmutter L. S. et al 1988). CANP 11, the high calcium threshold CANP is more restricted to glia (Hamakubo T. et al 1986). Calspastatin levels are lower in brain than in other tissues (Blomgren K. et al 1989).

Cathepsin B

Cathepsin B activity is reduced in Batten's Disease, a neuronal ceroid lipofuscinosis probably as a secondary consequence of accumulation of aldehydes or peroxides (Dawson G. et al 1987, 1988). Injection of thiol protease inhibitor leupeptin causes deposition of a lipofuscin like pigment with a high dolichol content.

Serine Endopeptidases

A serine endopeptidase inactivating cholecystokinin was identified in rat cerebral cortex (Rose C et al 1988). Its distribution in central nervous system has not been described. Abraham et al 1991 identified a calcium activated serine protease of molecular weight 20–35 KD capable of cleaving the methionine aspartate bond at the amino terminal cleavage site of beta protein of Alzheimer's disease cerebrovascular and plaque amyloid whilst observing that cathepsin G and a metal dependent cysteine protease also cleave this site.

Significance of divalent metal dependent enzymes in dementia pathology

Metal dependent endopeptidases such as the physiological precursor cleaving peptidases i.e. non lysosomal proteases, and calpains are activated by free metals in vivo. They can be implicated in the pathological changes of dementias, including beta amyloid and neurofibrillary tangle formation, and demyelination. The molecules involved in generating Lewy bodies, Hirano bodies, Pick bodies, and granulovacuolar degeneration are not known at the present time. Brain copper levels are highest in locus coeruleus, substantia nigra, putamen and globus pallidum respectively. Brain iron levels are highest in globus pallidum, putamen and substantia nigra respectively. Release of metals at particular subcellular sites is likely a common event in the pathogenesis of Alzheimer's, Parkinsonian, Batten's, Pick's dementias and dialysis aluminum induced encephalopathy. Agents which influence subcellular compartmentation and distribution of divalent metals will offer therapeutic prospects in preventing these pathologies. Enzyme inhibition of pre aspartate proteases may not be therapeutically practicable as these proteases serve physiological functions. Regulation of the peptide precursor cleaving enzyme activities by control of free metal levels is an interesting therapeutic avenue. Their significance in dementia pathogenesis is likely due to the absence of other enzyme classes, capable of cleaving at pre aspartate sites.

Manganese Miners Parkinsonism, Wilson's Disease and Dialysis Induced Encephalopathy Alzheimer's amyloid formation, neurofibrillary tangle and demyelination events are linked to divalent metals as described above. However in contrast to the three stages of disease development in Parkinson's Disease, Alzheimer's Disease and Lou Gehrig's Disease described in the model below, Manganese Miner's Parkinsonism and Wilson's Disease and Dialysis Induced Aluminum Encephalopathy do not include plaques, tangles and demyelination. Hence copper, manganese and aluminum overload are not linked to plaque and tangle formation and demyelination.

In Wilson's disease excess free copper in the serum, resulting from an inherited absence of the copper binding protein caeruloplasmin, becomes deposited in the brain and liver starting in early life. Parkinson's Disease, Alzheimer's Disease, Lou Gehrig's Disease, Olivopontine Cerebellar Atrophy, Binswanger's Disease, Cerebral Amyloid Angiopathy and Hereditary Cerebral Hemorrhage Dutch Type are not associated with an inherited deficiency of caeruloplasmin or other metal binding proteins. Cell death in Wilson's Disease results from direct cuprotoxic effects such as the inhibition of Krebs cycle enzymes. Both brain and liver copper levels are very high in untreated and even in successfully treated patients remain substantially above normal. Wilson's Disease responds to any type of copper chelates, unithiols, dithiols, tetramines and zinc as a copper displacement therapy. Therapeutic effect in terms of cupruresis and decrease in tissue copper levels occurs over days to weeks. Changes in receptor density of dopamine receptor subtypes (Schlaug D. et al), are not specific to Wilson's Disease and occur for example in Schizophrenia and Huntington's Disease. An increase in receptor subtype density could occur with a decreased, unchanged or increased dopamine level depending upon the underlying disease state.

In Parkinson's Disease, Alzheimer's Disease, Olivpontine Cerebellar Atrophy, Lou Gehrig's Disease, Binswanger's Disease and Cerebral Amyloid Angiopathy copper is not deposited in pericapillary areas. The pathological findings of Parkinson's Disease, Post Encephalitic Parkinsonism, Alzheimer's Disease, Olivpontine Cerebellar Atrophy, Lou Gehrig's Disease and Cerebral Amyloid Angiopathy include neurofibrillary tangles, amyloid plaques, granulovacuolar degeneration, Hirano bodies, Lewy bodies, Bumina bodies, demyelination and changes in brain enkephalin distribution. These changes are not observed in Wilson's Disease. Also Wilson's Disease is not associated with sensitivity to xenobiotics, whereas xenobiotics mimic and promote MPTP damage and have caused motor damage in mammals and man. Metals, such as iron, zinc, lead, cobalt, mercury or nickel do not cause the pathological changes of Wilson's Disease or Manganese Miner's Parkinsonism.

I. Free Radical 'Producing' and 'Protective' Enzymes

In Parkinson's disease catalase, reduced glutathione and glutathione peroxidase are also reduced (Ambani A. et al., Perry T. L. et al.) . Levels of reduced glutathione are very low in the substantia nigra of Parkinson's Disease patients, the normal nigra being a nucleus having low levels of reduced glutathione as compared to other human brain nuclei (Perry T. L. et al). Spermidine binds glutathione and age dependent loss of polyamines may decrease glutathione levels (Dubin D. T. 1959). Human caudate and putamen contain lower levels of spermidine than other brain areas and also a lower spermidine spermine ratio (Kremzner L. T.). In liver spermidine levels decrease during aging whereas spermine levels increase slightly, thus the ratio of spermidine to spermine decreases. However in brain the ratio increases as spermine levels decrease more than those of spermidine (Janne J. 1964).

Peroxidase activity in the substantia nigra, caudate and putamen is decreased as is catalase activity in the substantia nigra and putamen of Parkinsonian brains (Ambani A. et al). Cysteine required for glutathione synthesis may be depleted in dopaminergic neurones by pheomelanin which is being polymerized to neuromelanin (Prota G.). This imbalance may account for the increased redox stress associated with melanin synthesis in dopaminergic neurons (Seals R. C.). In the human brain glutathione peroxidase and glutathione reductase activities decrease with age (Marttila R. J. et al 1988).

High levels of CuZn SOD were demonstrated immunohistochemically in the large pyramidal cells of control and Alzheimer's disease patients brains (Delacourte A. et al 1988). The localization of the superoxide dismutase gene on chromosome twenty one and the early occurrence of Alzheimer's Disease in Down's syndrome suggest that superoxide dismutase activity and hydrogen peroxide formation may contribute to Alzheimer's pathogenesis. Also the neurones containing high levels of NADPH diaphorase are relatively spared in neonatal hypoxia and hypoglycemia but are affected in Alzheimer's disease. The increase in platelet membrane fluidity, noted in a subgroup of Alzheimer's disease patients, possibly due to dysregulation of platelet membrane biosynthesis is not associated with a higher erythrocyte level of superoxide dismutase (Zubenko G. S. et al 1989).

Superoxide is an inhibitor of catalase and glutathione peroxidase. Superoxide and hydroxyl radicals inhibit catalase, hydrogen peroxide and hydroxyl radicals inhibit glutathione peroxidase and hydrogen peroxide inhibits superoxide dismutase (Pigeolet E et al).

The enzymatic system in the basal ganglia operates within the following constraints; Age dependent and disease associated decline of the enzymes activities which remove hydrogen peroxide occurs especially in capillaries and therefore the capacity of the protective enzymes may be overrun by over activating copper and manganese dependent superoxide dismutases. The enzymes are active only within limited ranges as excess substrate or product will inhibit them.

Summary of Redox Environment in Parkinson's Disease, MPTP Parkinsonism and Guamanian Parkinsonian Dementia The phenomenology of Parkinson's disease includes excess oxidized iron and copper displacement. The physiological framework of the melanin and lipofuscin containing nuclei with low levels of glutathione peroxidase and catalase which enzymes are inhibited by excess of superoxide substrate or products indicates that only limited shifts of redox activity in either direction are permissible. NADPH diaphorase may protect these nuclei from oxidative stress as in neonatal anoxia but renders them more vulnerable to reducing agents. Superoxide and hydroxyl radicals inhibit catalase, hydrogen peroxide and hydroxyl radicals inhibit glutathione peroxidase and hydrogen peroxide inhibits superoxide dismutase (Pigeolet E et al).

Zinc displaced a redox metal and was effective in preventing paraquat toxicity in $E.\ coli$ (Korbashi P. et. al.), and histidine was successful in preventing MPP+ induced damage in $E.\ coli$ (Haskel Y. et. al). Diethylthiocarbamate, a superoxide dismutase inhibitor promoted MPTP effect of decreasing dopamine levels in mouse striatum (Corsini P. et. al.). Conversely, the toxicity of MPTP in hepatocytes was not increased by 1,3-bis (2 chloroethyl)-1-nitrosourea (BCNU) addition (Smith M. et. al.), and desferoxamine and penicillamine were not effective in preventing MPTP toxicity in isolated hepatocytes (Smith M. et. al.) and in Rana pipiens (Barbeau A. et. al. 1985b). Also MPTP and MPP+ did not cause lipid peroxidation in isolated hepatocytes whereas MPDP+ did (Ekstrom G. et al).

Metal displacement by zinc and metal binding by histidine can antagonize MPTP toxicity in bacterial cultures. Reducing agents and superoxide dismutase inhibitors and agents which mobilize copper such as the iron chelate desferoxamine promote MPTP toxicity.

Smith and Ekstrom's work demonstrates that MPTP and MPP+ are reducing agents. Further it is evident that thiol containing compounds such as diethylthiocarbamate and penicillamine which act as reducing agents, diethylthiocarbamate being a superoxide dismutase inhibitor, decrease dopamine levels and compound the decrease in brain dopamine caused by MPTP.

Desferoxamine also reduced brain dopamine (Barbeau A. et al 1986). The neurotoxicity of desferoxamine is thought to result from copper mobilization.

Reductive stress is common to both MPP+ damage and human Guamanian Parkinsonian dementia. MPP+ toxicity is associated with calcium release from mitochondria (Frei B.). Mobilization of mitochondrial calcium may follow calcium entry into cells following NMDA receptor agonism. NMDA antagonists exhibit some success in preventing histological damage in the MPTP treated mouse substantia nigra (24 L. Turski et al). The order of potency in preventing MPTP damage was not related to quisqualate antagonism. The toxicity of B N methylamino-L-alanine, an amino acid found in cycad seeds (cycas circinalis) and associated with amyotrophic laterosclerosis and Guamanian Parkinsonian dementia and also Parkinsonism models, can also be prevented by 2 amino-7-phosphonoheptanoic acid (AP7) (Ross S. M. 1987a, 1987b) and MK801 (Zeevalk G. D. et al) glutamate A1 receptor antagonists. The reducing agent dithiothreitol increases NMDA receptor mediated cell death in retinal ganglion cells, indicating that the redox state of the cell influences the response to glutamate and calcium entry (Levy D. I.).

Pigmentation and Depigmentation caused by Oxidation and Reduction

Increased dopamine turnover occurs in surviving neurones in Parkinson's disease. The brain nuclei most susceptible to damage have a high metabolic rate, thus requiring high levels of mitochondrial enzyme turnover. They contain high levels of bound metals in oxidized and reduced forms, and in view of the low levels of protective enzymes, they have limited capacity to handle oxidative and reductive stresses. Providing that neurones can oxidize amine precursors, amines and their products to neuromelanin and maintain a net deposition rather than breakdown of melanin, they can continue to store metals. Even in the presence of some metal excess, catecholamine and indoleamine synthesis will increase as the production of the neuroamines is influenced by metal-dependent hydroxylation reactions. Surviving neurones in Parkinson's Disease exhibit increased dopamine turnover which is prompted by higher absolute levels of reduced iron though the ratio of oxidized and reduced iron is shifted towards oxidized iron (Riederer P. et al).

Neuromelanin deposition occurs gradually and is not detectable macroscopically until at least six years of age in humans. Increased neuromelanin deposition occurs during human aging. Dopamine, norepinephrine and epinephrine are oxidized by tyrosinase to form aminochrome, noradrenochrome and adrenochrome. Autoxidation of amines occurs via quinone intermediates which are cyclized to polymers of neuromelanin (Graham D. G. et al 1978a). Divalent iron and manganese increase the autoxidation of dopamine in vitro (Barbeau A. et al 1986).

Dopamine as a source of polyphenolic compounds was found to be much more cytotoxic to C1300 neuroblastoma cells than beta hydroxylated catecholamines norepinephrine and epinephrine, either because it was more rapidly oxidized within the cell or its quinone products were more reactive (Graham D. G. et al). The hydroxyquinone product of 6 hydroxydopamine is covalently bound to cysteinyl residues of glutathione (Liang Y. O. et al). Levels of pigmentation in the substantia nigra increase as the relationship of animals to man on the evolutionary scale becomes closer (Marsden C.). The rate of autoxidation varies inversely with the maximum lifespan of the species (Cutler R. G.).

The levels of iron in the substantia nigra, globus pallidus, red nucleus and putamen are the highest in human brain, and the levels of copper are highest in the locus coeruleus and substantia nigra; copper levels are also high in globus pallidus and putamen. These polymers may form a metal and electron sink and may release metals during depigmentation. Free iron and copper may also promote the activity of preaspartate proteases, seven of which are metalloendopeptidases, and calpain activity.

Mitochondrial Damage in Parkinson's Disease and Alzheimer's Disease

A. Mitochondrial Cytochromes

Platelet mitochondria of patients with idiopathic Parkinson's Disease have reduced complex I (NADH: ubiquinone oxidoreductase) activity (Parker W. D. 1989). Deficient platelet endoplasmic reticulum NADH—cytochrome c reductase activity occurs in Alzheimer's Disease (Zubenko G. S. et al 1989) and deficiency of cytochrome oxidase (complex IV) in platelet mitochondria of Alzheimer's Disease patients (Parker W. D. et al 1990). MPTP neurotoxin inhibits NADH dehydrogenase (Singer I. P. et al). Antibiotics such as chloramphenicol also inhibit mitochondrial NADH dehydrogenase activity.

Compounds such as methyl viologen, which remove electrons from the electron transport chain, cause motor effects and substantially reduce brain dopamine and norepinephrine levels after prolonged exposure.

B. Enkephalins in Parkinson's Disease

In Parkinson's Disease brains met and enkephalin levels are reduced in putamen and substantia nigra and ventral tegmental area. In the striatum met and leu enkephalin may be stored in the same neuron and derived from proenkephalin A. In the substantia nigra and ventral thalamic area met and leu enkephalin may not be stored in the same neuron or may not be derived from the same precursor. Proenkephalin B contains the sequence of proneodynorphin, dynorphin and leu enkephalin but not met enkephalin. Dynorphin and neoendorphin are present in high concentrations in the substantia nigra whereas dynorphin and neoendorphin are not in high concentrations in the striatum. Selective degeneration of Proenkephalin A pathways or neurons would explain why levels of both peptides are reduced in the striatum whereas only met enkephalin levels are affected in the substantia nigra (Taquet H.). As measured by D-ala-2met-5(3H) enkephalin amide binding, opiate receptor binding is reduced in the pars compacta of the substantia nigra in Parkinson's Disease. Enkephalinase activity is likewise reduced (Llorens-Cortes C. et al). MPTP treatment of rhesus monkeys selectively reduced met enkephalin concentrations in the substantia nigra without changing the concentrations of other peptides. Met enkephalin arg gly leu and proenkephalin B derived peptides alpha neoendorphin and dynorphin decreased in putamen, but met and leu enkephalin were not decreased in globus pallidum after MPTP treatment (Lamir N.).

C. Enkephalins and MPTP

The neurotoxin MPTP also diminishes substantia nigra met enkephalin levels in Rhesus monkeys. Correlation of enkephalin alterations with anatomical sites indicates a selective degeneration of Proenkephalin A pathways or their gene expression in Parkinson's Disease (Taquet H. 1983).

MPTP's capacity to produce Parkinsonism may be associated with its effects on opioid expression and enkephalin binding sites. Enkephalins influence turnover and release and dopamine, which in turn, affects basic metabolism in basal ganglia regions of the brain.

D. Cytocrophins

Given that MPTP, an opiate derivative induces a Parkinsonian syndrome and that proenkephalin A products are reduced in Parkinson's Disease, an endogenous opioid is a possible candidate for causing some of the pathophysiologic disturbances in Parkinson's disease. Enzymatic digestion of bovine cytochrome b yields a peptide, whose sequence Tyr, -Pro, -Phe, -Thr i.e. fragment 345–349 of human mitochondrial cytochrome b is called cytocrophin-4. It has opioid activity as measured against a range of opioids, in causing inhibition of electrically induced contractions of the guinea pig ileum myenteric plexus/longitudinal muscle preparation (Brantl V. et al). The same pentapeptide sequence Tyr, -Pro, -Phe, -Thr, -Ile is present in human mitochondrial cytochrome b (Anderson S. et al), but not in mouse mitochondrial cytochrome b (Bibb M. J. et al). These cytocrophin sequences are also present in human NADH-ubiquinone oxidoreductase, chain 4, (Complex 1) which activity is reduced in Parkinson's Disease.

Pathogenesis of Parkinson's Disease

The iron excess, the low scavenging enzyme activities, inhibition of mitochondrial metabolism, morphological damage to mitochondria and damage to enkephalinergic pathways in Parkinson's Disease result from mitochondrial DNA damage and proteolysis of non functional cytochromes translated therefrom. The mitochondrial DNA environment, its damage and lack of a pyrimidine dimer repair system predispose to the development of Parkinson's Disease. Plaque and tangle formation in Parkinson's Disease and Alzheimer's Disease resulting therefrom are caused by the release of iron, copper and calcium which activate metalloendopeptidases. The differing anatomical distribution of damage in postencephalitic Parkinsonism relates to the manner in which influenza virus affected nuclear DNA and protein synthesis.

Parkinson's Disease may result from age related DNA damage in mitochondria caused by accumulation of free radicals, xenobiotics, dopamine, quinones, radiation, and age related decline in polyamine levels. Copper is particularly active in promoting xenobiotic induced DNA base damage (Yourtee D. M. et al 1992). Paraquat and polyamines, putrescine and spermidine show reciprocal competitive inhibition of uptake. This indicates that paraquat uses the polyamine uptake system (Grabie V et al 1993). Mitochondrial DNA mutates up to seventeen times faster than nuclear DNA in coding sequences (Wallace D. G. et al 1987) and up to six times the rate of silent mutations (Lanave C. et al 1984, Miyata T. et al 1982). Mitochonhdria lack a pyrimidine dimer repair system (Clayton D. A. et al).

A 5000 base pair deletion has been observed in some areas of the brain during aging and in Parkinsonians (Ikebe S. et al). A single base pair mutation or deletion at any of several sites can cause complex I deficiency in mitochondrial myopathy patients (Holt I. J. et al). The significance of these deletions, though likely rare amongst all Parkinson's disease cases is that random DNA base damage can produce a similar pattern of disease.

Leucocytes from amyotrophic lateral sclerosis patients with onset in sixth and seventh decades show damage resistant DNA synthesis following exposure to alkylating agents (Lambert C. W. et al 1989). This variation was not evident in younger onset cases and may occur secondarily. Deficient DNA repair has been reported in fibroblasts of Alzheimer's disease patients (Li J. C. et al 1985).

Disturbance of cytochrome regulation would lead to the iron and opioid defects. Excessive transcription, excessive translation of a normal mitochondrial transcript or an abnormally sequenced or spliced one, or excessive intramitochondrial proteolysis would serve as a source of raised intramitochondrial iron, raised intracellular iron and an endogenous opioid, cytocrophin.

Free iron levels in body fluids are of the order of 10–18M. Most iron in serum is bound to transferrin and the uptake of iron into cells is dependent on the activity of transferrin receptors. (Testa U.).

Raised iron levels promote the oxidation of catecholamines via quinone intermediates and free radical toxicity. The endogenous opioid may cause suppression of proenkephalin A transcription or influence its post transcriptional regulation, and also affect dopamine and other amine storage in vesicles and post synaptic effect.

Inhibition of mitochondrial cytochromes by blockade of mitochondrial transcription or mitochondrial translation should produce a shift in redox state to net reduction and depigmentation. Several xenobiotics were tested below; rifampicin, ethidium bromide, chloramphenicol and oxytetracycline.

Proteins and Messenger Ribonucleic Acids Changes In Parkinson's Disease

Gliosis is a constant finding in idiopathic Parkinsonism and demelanization of nigral neurons is commonly seen even when no loss of neurons is observed (Friede R.). A significant increase in aberrant messenger RNA is noted in glia early in the disease and a similar increase in neuronal messenger RNAs is observed later in the disease (Gomirato G. et al). The proportion of adenine in RNA of affected neuroglia increases and that of guanine and uracil decreases. The increase in messenger RNA is inversely proportional to melanin content in nigral neurons of Parkinsonian patients who died during the early stages of the disease. Surviving motor neurons in amyotrophic lateral sclerosis contain inclusions—Bumina bodies which are high in ribonucleic acid levels, and which are Lewy body-like or eosinophilic (Chou S. M. 1979).

An abnormal electrophoretic pattern of proteins in the erythrocytes of Parkinsonian patients has been claimed, leading to the suggestion that Parkinsonism may involve dysfunction of protein synthesis in glia resulting in biochemical and functional dedifferentiation (Weisberger A. S. et al). Mitochondrial DNA, rRNA, mRNA and protein synthesis increase in response to metabolic requirements as for example was demonstrated with mitochondrial cytochrome b in muscle tissue in response to contractile activity (Williams S. R. 1986). The increase in copy number was greater than occurred with nuclear genes and the proportions of 16s rRNA and 12S r RNA were unchanged (Williams S. et al 1986). Chloramphenicol increases mitochondrial RNA synthesis, inhibits mitochondrial protein synthesis and reduces mitochondrial NADH dehydrogenase activity. On the basis that chloramphenicol inhibits protein synthesis in proliferating cells (Weisberger A. S. et al), a non controlled trial of chloramphenicol 1.5 to 2.0 grams daily over a six week period was done in Parkinsonian patients. Clinical improvement in rigidity and dyskinesia and subsequently tremor in Parkinsonian patients commencing within four to seventeen days of onset of therapy, with the improvement increasing over ten to twenty eight days following its first becoming evident to the physician or patient (Steffanis G. N. et al). If reduction of cytochrome turnover has a beneficial effect in controlling the disease process this is mitigated by the inhibition of NADH dehydrogenase and extra detoxifying demands necessitated by chloramphenicol.

MPTP Parkinsonism Compared with Idiopathic Parkinsonism

The MPTP model of Parkinsonism produces opioid changes in brain which are not identical to those of Parkinson's Disease. MPP+ in mitochondria and cytosol acts as a reducing agent, obviating the need for release of ferrous iron release from cytochromes. The free radical can influence enkephalin activity, withdraw electrons from the electron transport chain and bind or release metals. Thus in producing opioid pathway damage, interference with electron transfer reactions, cytochrome inhibition, ATP depletion, altering the availability of redox metals it rapidly mimics the downstream defects of Parkinson's Disease without causing DNA damage or a transcriptional defect. However depletion of adenosine triphosphate and a rise in adenosine diphosphate levels increases mitochondrial translation rate, this being a homeostatic regulatory mechanism. Lewy bodies are absent. However the attenuated administration of MPTP to monkeys may result in immature Lewy body type pathology. They contained randomly oriented filaments or tubules resembling neurotubules. (Forno L. S. et al 1988). Though not producing a Parkinsonian syndrome in rodents it is cytotoxic in high doses. Inducibility of MPTP Parkinsonism in different species depends on their level of melanization, and the extent of loss of glutathione peroxidase and catalase during aging.

Guamanian Parkinsonian Dementia and the NMDA Receptor

MPP+ toxicity is associated with calcium release from mitochondria (Frei B.). Mobilization of mitochondrial calcium may follow calcium entry into cells following NMDA receptor agonism. NMDA antagonists exhibit some success in preventing histological damage in the MPTP treated mouse substantia nigra (24 L. Turski et al). The order of potency in preventing MPTP damage was not related to quisqualate antagonism. The toxicity of B N methylamino-L-alanine, an amino acid found in cycad seeds (cycas circinalis) and associated with amyotrophic laterosclerosis and Guamanian Parkinsonian dementia and also Parkinsonism models, can also be prevented by 2 amino-7-phosphonoheptanoic acid (AP7) (Ross S. M. 1987a, 1987b) and MK801 (Zeevalk G. D. et al) glutamate A1 receptor antagonists. The reducing agent dithiothreitol increases NMDA receptor mediated cell death in retinal ganglion cells, indicating that the redox state of the cell influences the response to glutamate and calcium entry (Levy D. I.).

NMDA Receptors and Polyamines

Polyamines have biphasic actions on the NMDA receptor, agonistic at lower doses and antagonistic at higher doses, the ranges and intensity of agonism and antagonism varying with chain length and charge distribution around the terminal nitrogen atoms. Spermine increases the activity of NMDA receptors in the hippocampus. There was a 3.5 fold increase in apparent affinity for glycine in the presence of 1 mM spermine and an increase in maximal response to NMDA. Voltage dependent block occurs and is likely due to binding of polyamine within the ion channel, (3H) MK801 site (Beneviste M et al 1993). Other polyamines such as putrescine inhibit spermine induced potentiation of the NMDA response (McGurk J. F. 1990).

Copper and Opiate Receptors

Cupric ion, a thiol oxidant causes naloxone reversible analgesia when injected intracerebroventricularly in mice. Dithiothreitol, a thiol reductant reverses the analgesia but has no effect in the oxidised form (Mazullo G. et al 1980). A glutathione copper complex in human erythrocytes inhibits opiate receptors. Copper converts high affinity to low affinity opiate sites, this being a necessary step in the activation and coupling of the receptor effector system (Sadee W. et al 1982). Copper, cadmium and mercury inhibit the binding of opioid agonists to mu receptors more than to delta receptors. Zinc inhibits mu receptor binding whereas delta and kappa receptors are insensitive to zinc. Magnesium and manganese stimulate binding to these receptors in rat cerebral cortex (Tejwani G. A. et al 1990). Zinc and copper at micromolar concentration reduce the number and affinity of enkephalin sites in rat brain (Ogawa N. et al 1985).

Polyamines and Protein Kinase C

Polyamines such as spermine can inhibit the catalytic domain of protein kinase C optimally at a concentration of 5 nM. (Mezetti G. et al 1988). Inhibition of phosphorylation towards histone is non competitive and results from cationic polyamines binding to phospholipids. Triethylene tetramine also inhibits binding of protein kinase C to phospholipid phosphatidylserine (Moruzzi M. S. et al 1990) It seems that positively charged terminal amino groups, an appropriate aliphatic side chain, suitable spacing between the internal nitrogen atoms and the intramolecular hydrophobicity are the necessary structural requirements. Spermine inhibits the formation of complexes between protein kinase C and membranes when calcium concentration is below 0.1 micromolar. At higher calcium concentrations spermine influences the ratio between enzymes molecules bound reversibly and irreversibly to the membrane (Moruzzi et al 1995). Copper inhibits protein kinase C with an IC 50 of approximately 30 micromolar. The inhibition is overcome by increasing the concentration of phosphatidylserine (Speizer L. A. et al).

Polyamines and Neuronal Regeneration

Spermine, spermidine and putrescine promote axonal regeneration of lesioned hippocampal neurons (Chu P et al.). Putrescine, spermine and spermidine injected subcutaneously into rats increased immunohistochemically detectable nerve growth factor (Gilad G. et al). Transgenic mice overexpressing ornithine decarboylase, which had high tissue putrescine levels were found on Northern blot analysis to have elevated mRNA levels of brain-derived neuronotrophic factor (BDNF), nerve growth factor (NGF), and neurotrophin-3 (NT-3) in hippocampus (Reeben M. et al).

Copper and Cholinergic Receptors

Copper at 3 micromolar concentration diminished the number of binding sites for (3H)-1-quinuclidinyl benzilate by 40–50 percent with an increase in affinity, and a decline in agonist affinity at the muscarinic sites. 2,2,2 tetramine reversed the effects of copper. Penicillamine caused similar effects to copper, probably by forming a disulphide bond with a sulfhydryl group (Farrar et al 1984). Copper increased the affinity of M1 and M2 agonists in rat hippocampus and cortex without affecting the affinity of muscarinic antagonists (Fisher A. et al) and in bovine brain (Baron B et al 1984). Copper deficiency decreased the numbers and affinity of muscarinic cholinergic receptors in rat brain (Farrar et al 1985).

SUMMARY OF THE INVENTION

This invention results from an attempt to look beyond traditional substance replacement therapies in the treatment of degenerative neurological disorders such as dopamine replacement through L Dopa therapy, increasing acetylcholine at post synaptic sites by using anticholinesterase drugs in treating Alzheimer's disease or the supply of growth factors or diffusible neuropeptides such as substance P via cell grafting in treating Parkinson's Disease and Alzheimer's disease.

Instead, the invention is directed to the intrinsic regulation of cellular activities in Parkinson's Disease, Alzheimer's Disease, Guamanian Parkinsonian Dementia, Amyotrophic Lateral Sclerosis, Olivopontine Cerebellar Atrophy, Hereditary Cerebral Hemorrhage—Dutch Type, Amyloid Angiopathy, Batten's Disease, and in the neuronal complications of Binswanger's Disease. An understanding is derived of why particular neurons are primary targets of damage in these diseases, a mechanism of progression from Parkinson's disease to Alzheimer's disease and how differing etiologic events determine the patterns of damage in Parkinson's disease and Alzheimer's disease and Batten's disease versus the relative importance of later events in the cascade in the pathogenesis of Amyotrophic Lateral Sclerosis (Lou Gehrig's Disease) and Guamanian Parkinsonian Dementia. Further understanding is gained of the steps at which diagnostic tests could be developed and where therapy can be employed.

Cascade of Events in Pathogenesis

In Parkinson's Disease mitochondrial DNA is damaged by dopamine and xenobiotics in the presence of reduced levels of naturally occurring polyamines. Polyamines protect DNA from damage by organic molecules by steric interactions. Polyamines competitively block the uptake of xenobiotics. They also induce transcription of growth factors such as nerve growth factor, brain derived neuronotrophic factor. Polyamines regulate the activity NMDA receptor and affect the level of agonism or antagonism at the MK801 ion channel. Polyamines regulate redox homeostasis by binding glutathione. These primary deficits associated with polyamine deficiency cause the dedifferentiation processes of these disease via the changes in growth factor levels or ratios, the rapid entry of calcium via the MK801 ion channel and the metabolic consequences by damaged RNA transcripts causing production of defective cytochromes.

Secondarily defective cytochromes are proteolysed and release enkephalin by products and also release free iron into the mitochondrial matrix. The iron is leached from damaged calcium laden mitochondria into the cytosol of the neurons. NMDA receptor activation causes calcium entry into cells.

Thirdly gross elevation of the free level of a metal such as iron causes displacement of other metals such as copper, nickel, cobalt and lead from sites where they are bound. One or more of these metals overactivate preasapatate proteases which can produce Beta amyloid and tangle associated proteins. In Parkinson's Disease and Alzheimer's Disease there is an increase in free copper levels in the absence of an absolute increase in copper levels or more likely an actual decrease in total tissue copper levels due to its loss in the cerebrospinal fluid. The free copper will activate amine oxidase, tyrosinase, copper zinc superoxide dismutase and monoamine oxidase B. The preaspartate proteases may be activated by several divalent metal ions including such as zinc, iron, calcium, cobalt. The literature on these proteases indicate that zinc and calcium are particularly likely. Given a role for divalent metals in activating pre aspartate proteases and amyloid production as a tertiary event in this model, it is in concordance with the clinical situation whereby patients present with Parkinson's Disease and subsequently Alzheimer's Disease rather than the converse. In Guamanian Parkinsonian Dementia the plaque formation likewise follows motor neuron and Parkinsonian pathology.

More specifically, therapeutic compounds have multiple actions on this cascade of events extending from DNA damage to amyloid production;

a) Competitive inhibition of uptake of xenobiotics at the polyamine transport site, such organic molecules being a cause of DNA damage;

b) Limitation of mitochondrial DNA damage by removal of free copper, iron and nickel ions by the presence of an aliphatic tetramine;

c) Induction of nerve growth factor, brain derived neuronotrophic factor and neuronotrophin-3 gene transcription;

d) Regulation of affinity of NMDA receptors and blockade of the MK801 ion channel;

e) Binding and conservation of reduced glutathione;

f) Maintenance of the homeostasis of the redox environment in brain;

g) Induction of metallothionein;

h) Inhibition of protein kinase C;

i) Non toxic chelation of divalent metals in brain;

j) Regulation of activity of pre-aspartate proteases;

k) Inhibition of superoxide dismutase, amine oxidase, monoamine oxidase B;

l) Regulation of brain polyamine levels in dementias with maintenance of endogenous polyamine levels;

EXPERIMENTAL BACKGROUND

Figure 1:
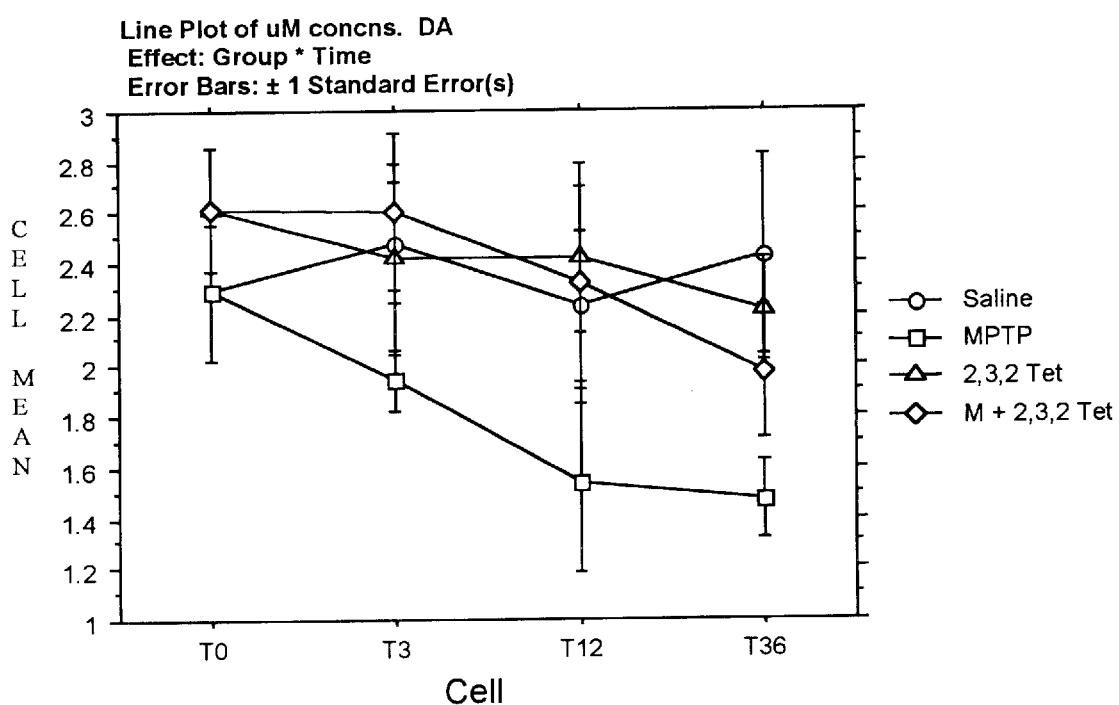
FIG. 1 is a graph showing brain dopamine concentrations in uM versus time in animals administered MPTP and 2,3,2 tetramine.
Figure 2:
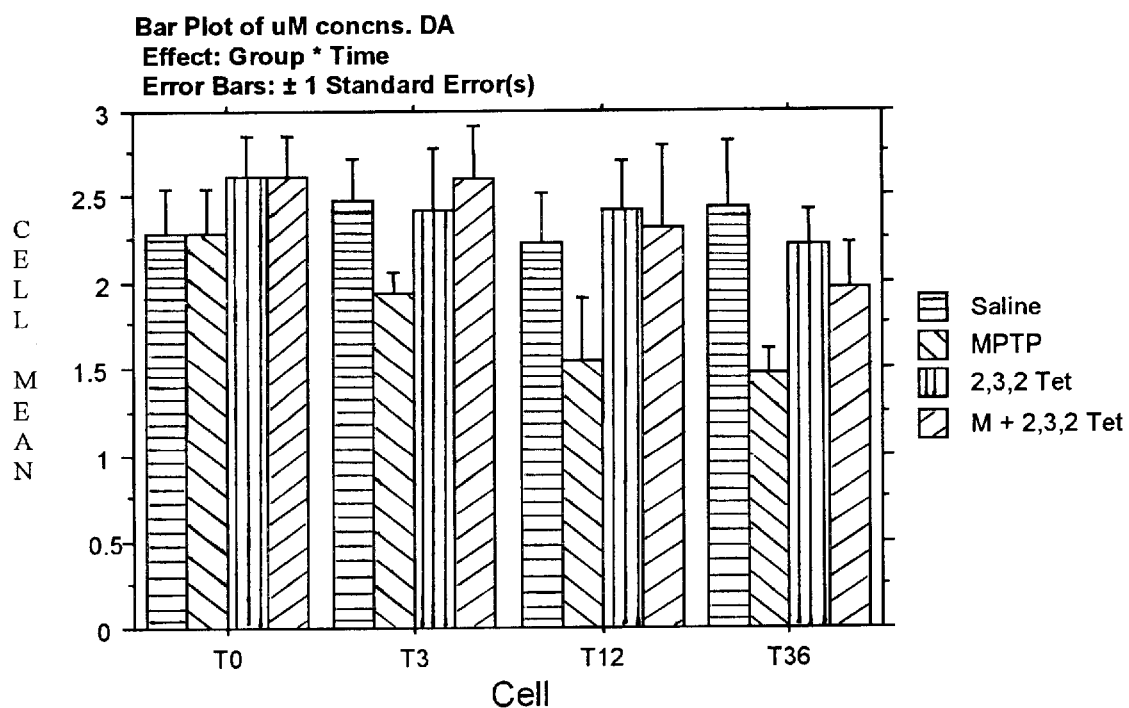
FIG. 2 is a bar chart of brain dopamine concentrations versus time following MPTP and 2,3,2 tetramine administration.
Figure 3:
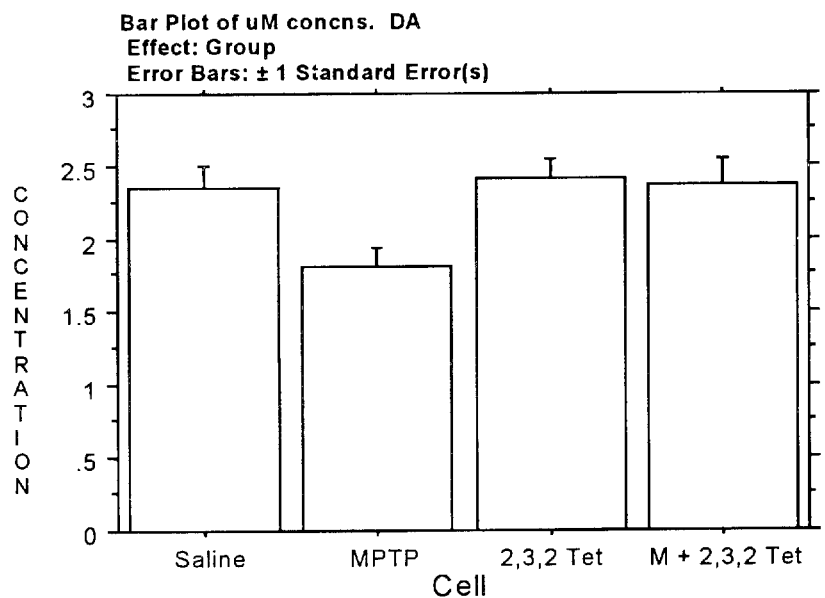
FIG. 3 is a bar chart of brain dopamine concentrations following MPTP and 2,3,2 tetramine administration.
Figure 4:
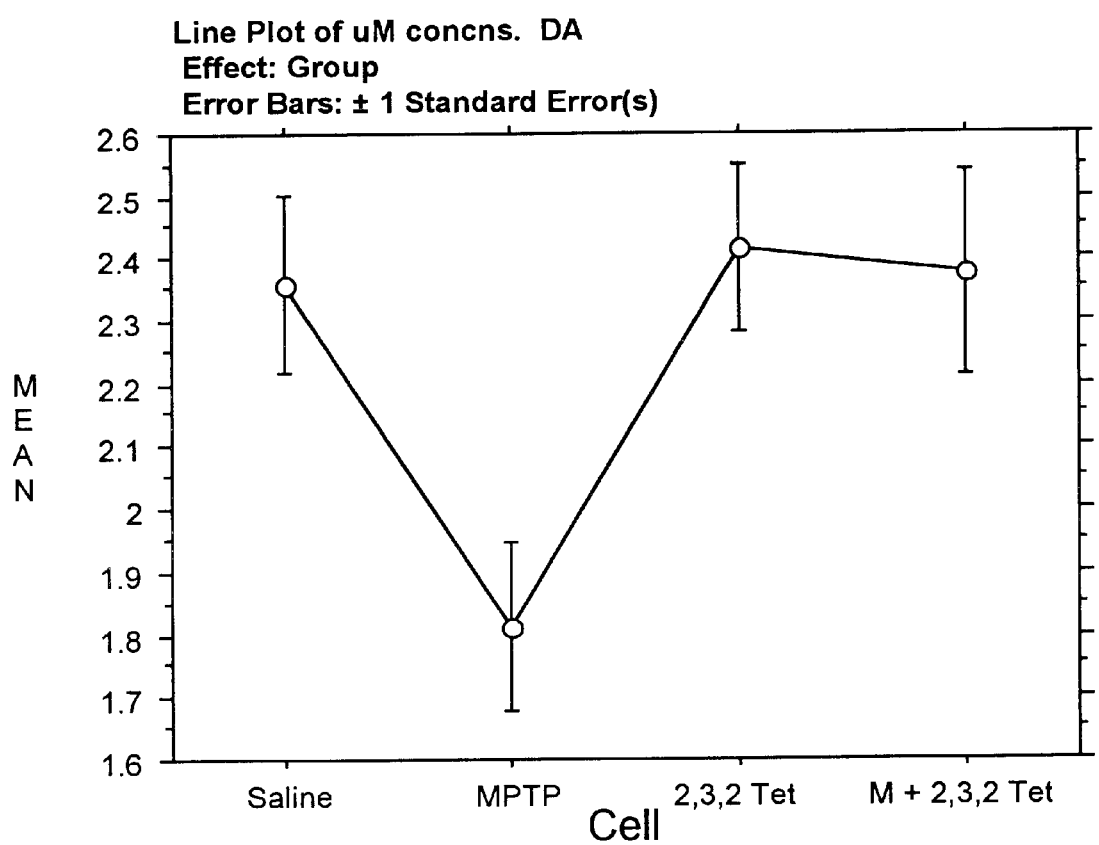
FIG. 4 is a graph of brain dopamine concentrations following MPTP and 2,3,2 tetramine administration.
Figure 5:
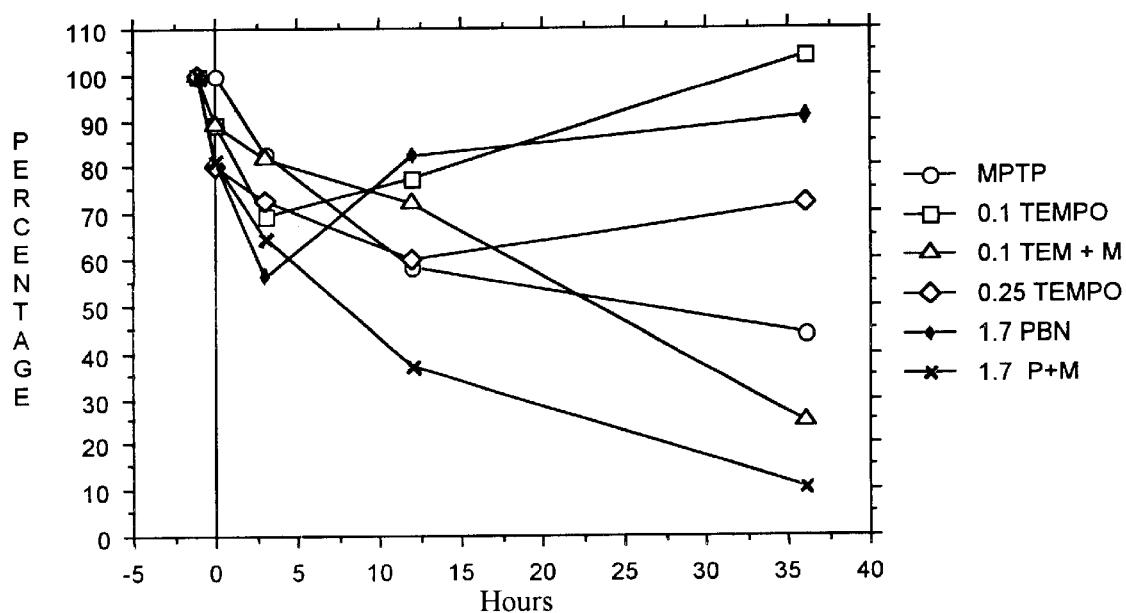
FIG. 5 is a graph of brain dopamine percentages versus time following MPTP, TEMPO and PBN administration.
Figure 6:
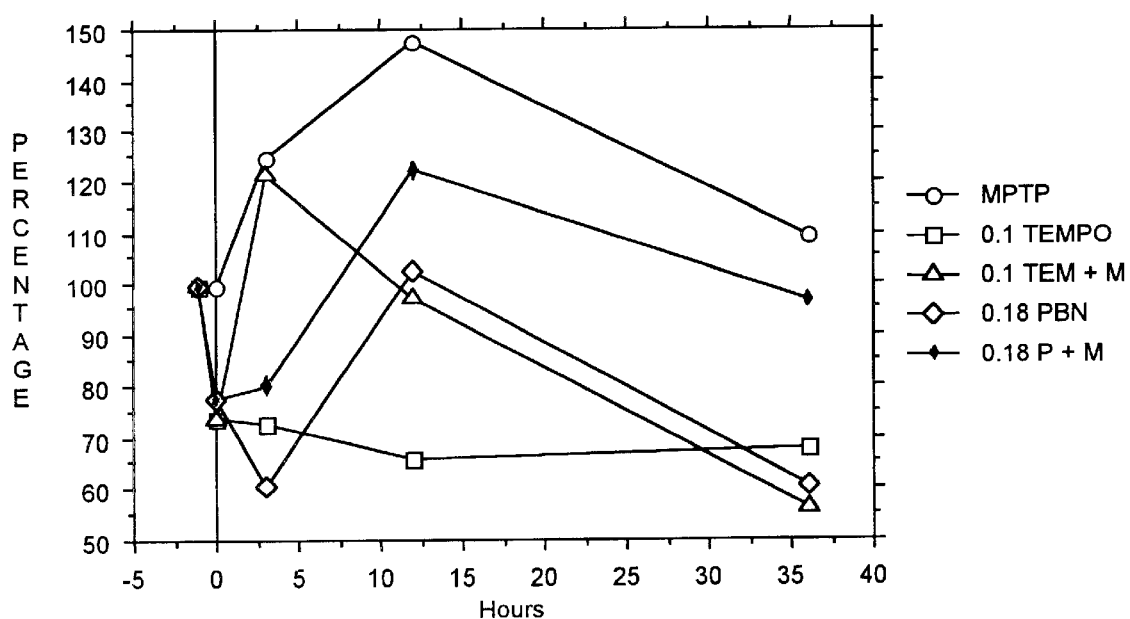
FIG. 6 is a graph of brain norepinephrine percentages versus time following MPTP, PBN and TEMPO administration.
Figure 7:
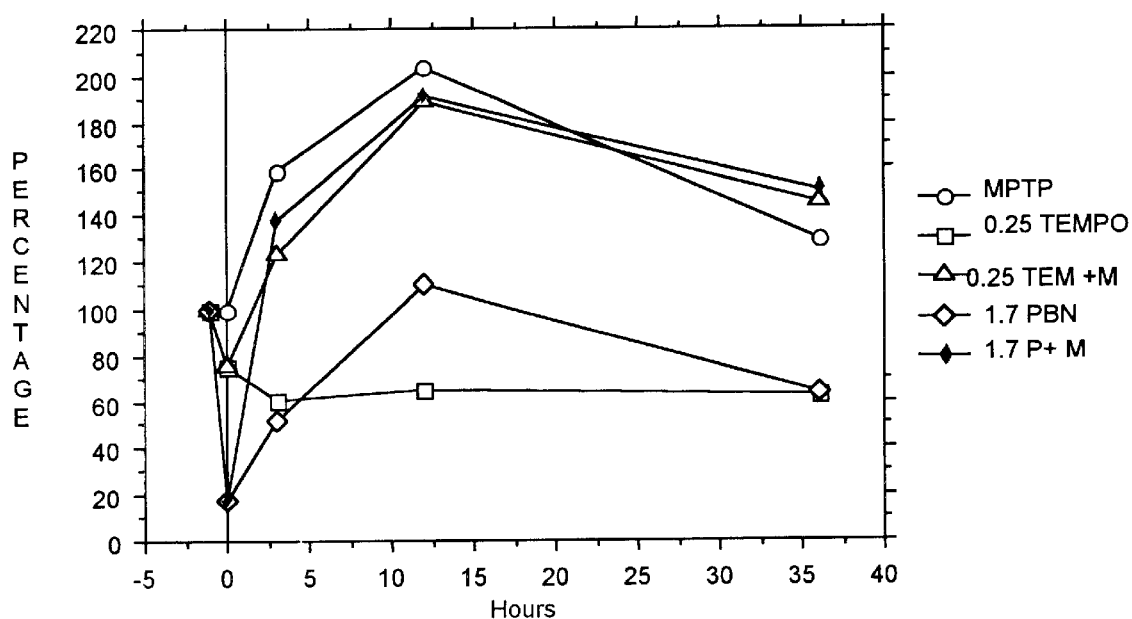
FIG. 7 is a graph of brain serotonin percentages versus time following MPTP, PBN and TEMPO administration.
Figure 8:
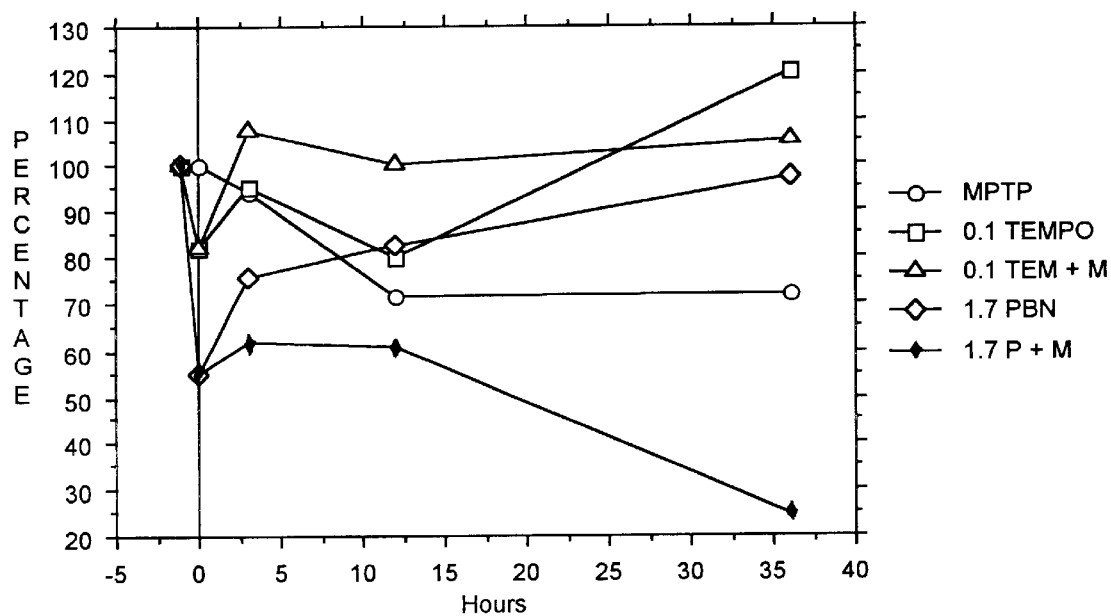
FIG. 8 is a grapah of brain epinephrine percentages versus time following MPTP, PBN and TEMPO administration.

Bradykinesia, rigidity and tremor occur in frog following MPTP injection in doses comparable to those causing effects in humans and monkeys (Barbeau A. et al 1985a. MPTP and paraquat cause rigidity, bradykinesia and tremor in frogs. Paraquat initially causes an increase in brain dopamine concentration and later a decrease (Barbeau A. et al 1985b). Motor effects were also observed herein with chloramphenicol.

The hyperpigmentation of aging precedes the depigmentation of dementia pathologies and MPTP also sequentially causes hperpigmentation and depigmentation. Pigmentation is an oxidative process requiring copper to activate tyrosinase. Removal of copper and or shift of redox state to net reduction should cause depigmentation without prior hyperpigmentation as was observed with spin trapping and spin labelling compounds.

Given the constraints evident from the use of xenobiotics and chelates which disturb subcellular metal compartmentation and the inflexibility of the redox enzyme system, an effective compound would need to remove excess copper from tyrosinase, superoxide dismutase, monoamine oxidase B, amine oxidase and also the iron excess which displaces copper from storage sites in idiopathic Parkinsonism. It must not be a direct superoxide dismutase inhibitor or thiol containing reducing agent. Triethylene tetramine does reduce superoxide dismutase activity without oxidizing glutathione (Kelner M. J. et al 1989). Removal of excess metals and limiting polyamine degradation are probably the most effective means of preventing mitochondrial DNA damage and helping the fidelity of DNA base replication. Tetramines are promising compounds towards these requirements and thus were tested in this system. They have effects on copper, iron and nickel metabolism (Sunderman F. W et al 1976, Baselt R. C. et al 1977), are very effective chelators with low reported toxicity and also induce metallothionein synthesis.

Experimental Observations

MPTP has been shown by Barbeau et. al. to induce a Parkinsonian syndrome in Rana pipiens (Barbeau A. et al 1985b, 1986). This model, with similar doses of MPTP as employed previously 40 mg/Kg was used to confirm the previous observations on MPTP and catecholamines and extend them to observe indoleamines for which the Rana pipiens model was convenient and reproducible. Measurements of neuroamines over an intermediate time scale provided insights into MPTP neurotoxicity as distinct to non specific mechanisms of cell death observed in brief duration cell culture experiments.

Materials and Methods

20–40 gram frogs (Rana pipiens) were maintained in a semi aquatic environment under humane conditions. Frogs were sacrificed humanely. Brain including medulla, was removed and stored at −70 degrees C. MPTP free base was dissolved in phosphate buffered saline and freshly prepared daily. Animals were administered a single dose of MPTP 40 mg/Kg intraperitoneally. Loading doses of metals, TEMPO, PBN, Xenobiotics, depigmenting agents or saline were administered one hour prior to MPTP. Six animals were used in each treatment and control group. Brain samples were sonicated in cold 0.1 MHClO4 containing 20 mg/ml 3,4-dihydroxybenzylamine. Homogenates were centrifuged at 15,000 r.p.m. for 15 minutes at 4 degrees C. Supernatants were injected directly into the HPLC chamber. High performance liquid chromatography was performed using a Rabbit Rainin system with Rheodyne injector. Fifteen neuroamines, precursors, and degradation products were measured at the 5 pmole level using the method of Wester, with the modification that 200 nM sodium phosphate buffer was utilized instead of sodium citrate buffer (Wester P. 1987). Brain metal levels were measured by a Zeeman atomic absorption spectrophotometer. Movements were rated according to a system previously employed (Barbeau A. et al 1985). Pigmentation was measured using a rating scale described by Hogben and Slome.

2,3,2 Tetramine (3,7-diazanonane-1,9-diamine)

2,3,2 Tetramine (2,3,2 tetraamine, 2,3,2 tetra-amine) has been synthesized since 1936 (Van Alpen J. 1936) and this class of tetramines has been used primarily in industry as curing agents for epoxy resins, in adhesives and coatings and as fungicides. A listing of compounds having structural relationships or exhibiting similar physical/chemical/biochemical behaviors, not meant to exclude others, is included later. In rats 2,3,2 tetramine and 2,2,2 tetramine (trien) have been found to be effective cupruretic agents, 2,3,2 being the more effective (Borthwick et al 1980). Its higher effectiveness relates in part to its having a 10,000 fold greater affinity for copper than 2,2,2 tetramine. The CuN4 chromophore in 2,3,2 tetramine is approximately planar in contrast with 2,2,2 tetramine. 2,2,2 tetramine has been used successfully in the treatment of Wilson's disease, including instances where penicillamine had to be discontinued due to its causing systemic lupus erythematosis (Walshe J. M. 1969, Harder H. et al 1977, and Walshe J. M. 1975).

2,3,2 Tetramine 2,3,2 Tetramine 1.2 mM dose preloading one hour prior to MPTP was completely effective in preventing MPTP induced dopamine loss twelve hours post MPTP injection and was partially protective at thirty six hours. See FIG. 1. 2,3,2 tetramine has a half life of three to four hours whereas MPTP is excreted over twenty four to forty eight hours. Dosing animals with 2,3,2 tetramine by intraperitoneal injection six hourly during the first twelve hours was insufficient to provide full protection at 36 hours. 2,3,2 tetramine had no deleterious effects on pigmentation or behavior by contrast with the iron chelate 1,2 diethyl-3-hydroxypyrid-4-one (CP94) which caused hyperpigmentation in some animals.

TABLE 1

Micromolar Brain Dopamine concentration following MPTP and 2,3,2 Tetramine

| | | Hours | | | |
|---|---|---|---|---|---|
| | | 0 | 3 | 12 | 36 |
| Saline | | 3.358 | 3.199 | 3.423 | 2.903 |
| | | 2.245 | 2.640 | 1.638 | 1.439 |
| | | 1.419 | 1.546 | 1.931 | 2.773 |
| | | 2.176 | 2.832 | 2.633 | 1.272 |
| | | 1.969 | 2.109 | 2.370 | 3.836 |
| | | 2.597 | 2.560 | 1.609 | 2.376 |
| Mean | | 2.294 | 2.481 | 2.268 | 2.433 |
| 2,3,2 | | 3.124 | 1.631 | 2.774 | 2.515 |
| Tetramine | | 2.690 | 3.971 | 3.552 | 2.072 |
| | | 3.091 | 1.462 | 2.395 | 2.242 |
| | | 1.585 | 2.779 | 1.972 | 2.972 |
| | | 2.307 | 2.185 | 1.479 | 1.951 |
| | | 2.901 | 2.470 | 2.370 | 1.564 |
| Mean | | 2.616 | 2.416 | 2.419 | 2.219 |
| MPTP | | 3.358 | 1.972 | 2.924 | 1.860 |
| | | 2.245 | 2.094 | 2.174 | 1.758 |
| | | 1.419 | 1.988 | 1.604 | 1.499 |
| | | 2.176 | 2.278 | 1.187 | 0.821 |
| | | 1.969 | 1.406 | 0.903 | 1.590 |
| | | 2.597 | 1.915 | 0.482 | 1.312 |
| Mean | | 2.294 | 1.942 | 1.546 | 1.473 |
| 2,3,2 | | 3.124 | 1.457 | 4.615 | 3.051 |
| Tetramine + MPTP | | 2.690 | 2.679 | 2.132 | 2.253 |
| | | 3.091 | 2.883 | 1.431 | 2.059 |
| | | 1.585 | 2.298 | 1.899 | 1.714 |
| | | 2.307 | 3.773 | 1.986 | 1.487 |
| | | 2.901 | 2.551 | 1.869 | 1.276 |
| Mean | | 2.616 | 2.607 | 2.921 | 1.973 |

Factoral Analysis of all samples in Table 1.
Bonferroni/Dunn of DA
Effect: Group
Significance Level: 5%

| | Mean Diff. | Crit. Diff | P-Value | |
|---|---|---|---|---|
| Saline, MPTP | .547 | .558 | .0097 | |
| Saline, 2,3,2 Tet | −.058 | .558 | .7799 | |
| Saline, 2,3,2 Tet + M | −.020 | .558 | .9237 | |
| MPTP, 2,3,2 Tet | −.605 | .558 | .0044 | S |
| M, 2,3,2 Tet + M | −.567 | .558 | .0075 | S |
| 2,3,2 Tet, 2,3,2 Tet. + M | .038 | .558 | .8543 | |

MPTP and 2,3,2 Tetramine are significantly different $p < 0.005$
MPTP and 2,3,2 Tetramine + MPTP groups are significantly different $p < 0.008$

TABLE 2

Percentage of Brain Dopamine following MPTP and 2,3,2 Tetramine

| | Hours | | | |
|---|---|---|---|---|
| | 0 | 3 | 12 | 36 |
| Saline | 100 | 100 | 100 | 100 |
| 2,3,2 Tetramine | 114 | 97 | 107 | 91 |

TABLE 2-continued

Percentage of Brain Dopamine following MPTP and 2,3,2 Tetramine

| | Hours | | | |
|---|---|---|---|---|
| | 0 | 3 | 12 | 36 |
| MPTP | 100 | 78 | 68 | 61 |
| 2,3,2 Tetramine + MPTP | 114 | 105 | 102 | 81 |

2,3,2 Tetramine + MPTP and MPTP are significantly different P-value 0.01 at 95% confidence level Brain Metal Levels Rana pipiens were injected intraperitoneally once daily over five days with metals and chelators and brain iron, copper and manganese levels determined by atomic absorption spectrophotometry.

15 mM FeNTA (nitrilotriacetic acid) increased brain iron levels to 354 nmoles/gm wet weight, 179% of saline controls.

15 mM NTA increased brain iron levels to 270 nmoles/gm wet weight, 136% of saline controls.

FeNTA raised brain copper levels to 56 nmoles gm. wet weight 169% of controls.

NTA alone raised brain copper levels to 45 nmoles/gm. wet weight, 137% of saline controls.

15 mM MnNTA lowered copper levels to 25 nmoles/gm. wet weight 76% of controls.

MnNTA increased brain manganese to 15 nmoles/gm wet weight, 157% of controls.

1.2 mM. 2,3,2 Tetramine, 9 mM. desferoxamine and 1.8 mM copper tris did not noticeably change brain iron, copper or manganese levels.

TABLE 2

Iron, Copper and Manganese levels in Brain following 5 Day Loading with Metals and Chelates

| | Brain Metal level in nMoles/ Gm Wet Weight | | |
|---|---|---|---|
| | Fe | Cu | Mn |
| Saline | 198 | 33 | 9.8 |
| Tris | 150 | 42 | 5.9 |
| CuTris | 166 | 35 | 5.2 |
| 2,3,2 T | 242 | 41 | 8.6 |
| NTA | 270 | 45 | 8.4 |
| FeNTA | 354 | 56 | 9.4 |
| DFO | 178 | 31 | 8.2 |
| MnNTA | 166 | 25 | 15.4 |

Loading animals with iron caused tremor in some animals. Copper loading caused hyperpigmentation and rigidity. Iron loading induced tremor and copper loading induced rigidity and bradykinesia.

Xenobiotics

Inhibition of mitochondrial cytochromes by blockade of mitochondrial transcription or mitochondrial translation should produce a shift in redox state to net reduction and depigmentation. The xenobiotics used, rifampicin, ethidium bromide, chloramphenicol and oxytetracycline cause dopamine depletion when used alone or in combination with MPTP and they also cause depigmentation. As with MPTP, depigmentation was frequently preceded by hyperpigmentation, especially with chloramphenicol. This presumably relates to metal displacement initially followed by shift in redox milieu to reductive state when cytochrome levels are lowered by chloramphenicol. Chloramphenicol 31 mg/Kg daily in combination with MPTP lowered dopamine to 33% of control values in 24 hours. Chloramphenicol 400 mg/Kg alone lowered dopamine to 38% of control levels in 24 hours. By contrast rifampin and ethidium bromide caused more immediate depigmentation.

Spintrap/spinlabel compounds

The radical scavenging and reducing agents (in consequence of oxidizing redox metals) TEMPO and PBN were used as a further test of MPTP's behavior as a reducing or oxidizing compound. The effects of the xenobiotic MPTP alone and in combination with spin traps/spin labels TEMPO (2,2,6,6-tetramethylpiperidine-N-oxyl), at 0.1 mM, 0.25 mM and 1.0 mM doses, and PBN (N-tert-butyl-a-phenylnitrone), at 0.18 mM and 1.7 mM doses, preloading the animals one hour prior to MPTP administration, indicated their patterns of effects on these amine precursor hydroxylations. MPTP decreased dopamine levels, and increased norepinephrine and serotonin levels, whereas TEMPO and PBN decreased norepinephrine, serotonin and dopamine levels. Administered alone they reduced pigmentation density.

Dopamine levels in MPTP, TEMPO and PBN treated animals.

PBN in combination with MPTP dropped dopamine levels to about 10 percent of baseline. Toxicity was dose dependent and cumulative for both PBN and MPTP. TEMPO likewise decreased dopamine more than MPTP alone. TEMPO toxicity was less dose dependent.

TABLE 3

Mean Brain Dopamine Micromolar Concentrations versus Time

| | 0 | 3 | 12 | 36 |
|---|---|---|---|---|
| Saline | 2.495 | 2.477 | 2.214 | 2.067 |
| MPTP | 2.495 | 2.059 | 1.296 | 0.908 |
| 0.1 TEMPO | 2.230 | 1.722 | 1.722 | 2.152 |
| 0.1 T + MPTP | 2.230 | 2.029 | 1.601 | 0.519 |
| 0.25 TEMPO | 2.007 | 1.805 | 1.331 | 1.496 |
| 0.25 T + MPTP | 2.007 | 1.686 | 0.865 | 0.489 |
| 1.0 TEMPO | 5.689 | 2.432 | 2.056 | 1.053 |
| 1.0 T + MPTP | 5.689 | 2.907 | 1.445 | 1.425 |
| 0.18 PBN | 2.137 | 1.837 | 2.210 | 1.768 |
| 0.18 PBN + MPTP | 2.137 | 1.863 | 1.152 | 0.775 |
| 1.7 PBN | 2.026 | 1.400 | 1.825 | 1.879 |
| 1.7 PBN + MPTP | 2.026 | 1.600 | 0.822 | 0.215 |

MPTP 40 mg/Kg dose, TEMPO and PBN in millimolar concentrations, n = 6 per mean.

Norepinephrine levels in MPTP, TEMPO and PBN treated animals.

PBN at 0.18 mMolar partially reverses the MPTP effect of elevating norepinephrine by decreasing it to eighty percent at times less than four hours. This corresponds with the time of PBN maximal effect.

TEMPO 0.1 mMolar had little effect on MPTP induced norepinephrine elevation at 3 hours in contrast with PBN, but does lower norepinephrine to baseline by thirteen hours.

TABLE 4

Mean Brain Norepinephrine Micromolar Concentrations versus Time

|  | 0 | 3 | 12 | 36 |
|---|---|---|---|---|
| Saline | 3.067 | 2.508 | 2.069 | 2.644 |
| MPTP | 3.0673 | 3.3134 | 3.049 | 2.889 |
| 0.1 TEMPO | 2.260 | 1.829 | 1.367 | 1.800 |
| 0.1 T + MPTP | 2.260 | 3.051 | 2.013 | 1.488 |
| 0.25 TEMPO | 3.541 | 1.947 | 1.810 | 1.638 |
| 0.25 T + MPTP | 3.541 | 2.309 | 2.125 | 1.700 |
| 1.0 TEMPO | 3.873 | 6.235 | 5.269 | 4.302 |
| 1.0 T + MPTP | 3.873 | 1.873 | 1.992 | 1.695 |
| 0.18 PBN | 2.379 | 1.519 | 2.124 | 1.598 |
| 0.18 PBN + MPTP | 2.379 | 2.010 | 2.536 | 2.567 |
| 1.7 PBN | 1.360 | 1.594 | 1.989 | 2.428 |
| 1.7 PBN + MPTP | 1.360 | 1.622 | 1.183 | 0.230 |

MPTP 40 mg/Kg dose, TEMPO and PBN in millimolar concentrations, n = 6 per mean.

Serotonin levels in MPTP, TEMPO and PBN treated animals.

PBN at low and high doses in combination with MPTP was not protective against MPIP induced elevation in serotonin. Likewise TEMPO was not protective at low or high doses.

TABLE 5

Mean Brain Serotonin Micromolar Concentrations versus Time

|  | 0 | 3 | 12 | 36 |
|---|---|---|---|---|
| Saline | 9.479 | 12.183 | 8.010 | 11.339 |
| MPTP | 9.479 | 19.436 | 16.321 | 14.749 |
| 0.1 TEMPO | 8.954 | 7.322 | 6.507 | 13.571 |
| 0.1 T + MPTP | 8.954 | 17.775 | 17.279 | 15.579 |
| 0.25 TEMPO | 7.178 | 7.406 | 5.203 | 7.062 |
| 0.25 T + MPTP | 7.178 | 14.973 | 15.151 | 16.478 |
| 1.0 TEMPO | 9.617 | 12.289 | 6.936 | 5.874 |
| 1.0 T + MPTP | 9.617 | 8.036 | 4.386 | 4.548 |
| 0.18 PBN | 7.494 | 8.736 | 11.364 | 8.153 |
| 0.18 PBN + MPTP | 7.494 | 14.086 | 16.728 | 16.269 |
| 1.7 PBN | 1.704 | 6.408 | 8.814 | 7.254 |
| 1.7 PBN + MPTP | 1.704 | 16.838 | 15.290 | 17.084 |

MPTP 40 mg/Kg dose, TEMPO and PBN in millimolar concentrations, n = 6 per mean.

Epinephrine levels in MPTP, TEMPO and PBN treated animals.

Higher doses of PBN and TEMPO has additive effect with MPTP in lowering epinephrine at four and thirty seven hours. Lower doses of PBN and TEMPO minimize the MPTP induced loss of epinephrine. Though norepinephrine is elevated by MPTP during the first twelve hours, epinephrine levels decline from the beginning of MPTP exposure. This suggests that there is more precursor norepinephrine available when exposed to MPTP. However cell death is also occurring and levels of epinephrine are lowered by MPTP alone and MPTP in combination with TEMPO and PBN at the later times.

TABLE 6

Mean Brain Epinephrine Micromolar Concentrations versus Time

|  | 0 | 3 | 12 | 36 |
|---|---|---|---|---|
| Saline | 12.996 | 9.466 | 10.315 | 8.807 |
| MPTP | 12.996 | 8.953 | 7.389 | 6.367 |
| 0.1 TEMPO | 10.687 | 9.059 | 8.268 | 10.610 |
| 0.1 T + MPTP | 10.687 | 10.183 | 10.342 | 9.308 |
| 0.25 TEMPO | 10.868 | 9.245 | 7.167 | 6.532 |
| 0.25 T + MPTP | 10.868 | 8.639 | 6.587 | 6.904 |
| 1.0 TEMPO | 9.779 | 12.043 | 6.379 | 3.206 |
| 1.0 T + MPTP | 9.779 | 12.631 | 6.881 | 8.034 |
| 0.18 PBN | 9.775 | 7.390 | 10.330 | 8.036 |
| 0.18 PBN + MPTP | 9.775 | 7.904 | 8.348 | 11.283 |
| 1.7 PBN | 7.186 | 7.155 | 8.521 | 8.607 |
| 1.7 PBN + MPTP | 7.186 | 5.880 | 8.607 | 2.198 |

MPTP 40 mg/Kg dose, TEMPO and PBN in millimolar concentrations, n = 6 per mean.

The effects of PBN at the doses tested were acute and short lived. The TEMPO effects occurred at times later than those of PBN, but remained throughout the experiment. The actions of TEMPO and PBN do not appear to differ. Time related differences may reflect different pharmacokinetic patterns of two compounds with differing hydrophilic and lipophilic properties. Overall it is clear that TEMPO and MPTP had significant effects at approximately twelve hours, whereas PBN had marked effects on neuroamin e levels at one to four hours. The reduction in dopamine is dose dependent for TEMPO, and PBN did not reduce dopamine below baseline at the later time. An antagonistic effect against MPTP induced elevation of norepinephrine levels was evident at the low doses of both compounds, especially with PBN. This again emphasizes the importance of copper mobilization in the induction of Parkinsonism by MPTP.

Discussion

Tetramines

Dopamine levels in brain are vulnerable to many neurotoxins and xenobiotics. Its successful conservation by 2,3,2 Tetramine in vivo provides a therapeutic avenue in Parkinson's Disease and dementias involving similar pathogenetic events. The inability of iron chelators, penicillamine, anti oxidants to prevent dopamine loss and MPTP damage indicates that this family of compounds has a unique profile in actions such as mimicing an endogenous polyamine; prevention of DNA damage, altering agonism at NMDA and muscarinic cholinergic sites, induction of growth factors, induction of metallothionein, antagonising cellular uptake of xenobiotics, inhibition of protein kinase C, binding to glutathione, redistribution of metals between diverse storage pools and free metal levels in cytosol, reduction of the activities of pre aspartate proteases, amine oxidase, monoamine oxidase and superoxide dismutase.

Metal Distribution and Redox State

Iron entry and excretion from neurons depends upon transferrin receptors which can prevent excretion of excess iron when iron is released from intracellular sites. 2,3,2 tetramine did not greatly alter total levels of iron, copper or manganese in brain. Copper loading, which caused marked pigmentary and behavioral changes, and desferoxamine also did not alter total brain levels of iron, copper and manganese. Simple chelation is not effective in the MPTP model and actually enhances damage, in the case of thiols such as penicillamine by acting as reducing agents and with desferoxamine and CP94 by metal displacement. Barbeau A. et al. likewise observed that desferoxamine and penicillamine were neurotoxic when administered alone and in combination with MPTP. Specifically the augmentation of damage by reducing agents and spin traps which trap organic radicals and metals supports the observation that decreasing absolute metal levels and shift from oxidized to reduced states is damaging, homeostasis rather than extremes of oxidation or reduction being the cell's normal state. The NMDA receptor is activated in its reduced state. Thus redox homeostasis rather than preventing oxidative states is relevant to damage prevention. 2,3,2 tetramine in the MPTP model has effect on the immediate damage caused by MPTP with full conservation of dopamine during the initial hours. Thus the effect of 2,3,2 tetramine on steric protection of DNA from organic molecules, on the NMDA receptor, on blockade of xenobiotic uptake, and conservation of glutathione are primary aspects of its action as distinct to the longer timeframe of action of chelates which decrease metal levels over days to weeks.

Additionally the removal of iron or zinc may be beneficial to the treatment of Parkinson's Disease, Alzheimer's Disease and Lou Gehrig's Disease, given the excess iron in Parkinson's Disease brain and the excess iron and zinc in Alzheimer's Disease brain and their potential roles in activating pre asparatate proteases. Removal of cobalt, mercury, nickel, lead if present in excess may be helpful. Given that tissue copper levels are likely decreased due to the loss in cerebrospinal fluid, its removal from brain may not necessarily be a part of the therapeutic action. The net effect of 2,3,2 tetramine on the level of a divalent metal at a subcellular site is determined by the combination of its effects in transporting the metal in or out of the tissue, metallothionein induction and what effect it has on other metals which could displace the metal from bound sites.

L Dopa replacement therapy

Clinical treatment of Parkinsonism focuses on replacing defective dopamine levels by precursor dopa administration. Whilst it is notionally simple, the relative therapeutic effectiveness of L-dopa therapy in Parkinson's disease may be influenced by pre-existing increased dopamine turnover in surviving neurons, dopa's role as substrate for pigment formation and the actions of dopa as a metal chelate or translocator. Furthermore, brain indoleamines are reduced in some cases of Parkinson's Disease, as was observed here in this MPTP model at forty eight hours and later.

Metal dependence of amine producing and degradative enzymes

MPTP was shown to decrease dopamine, while increasing serotonin and norepinephrine. Reduced iron is rate limiting in the tyrosine hydroxylase reaction and copper is ineffective (Fitzpatrick P. F.). The four human isoforms of the enzyme require reduced iron for catalysis and are inhibited by nickel (Haavik J. et al). Both tyrosine hydroxylase and tryptophan hydroxylase are activated in a two step procedure by calcium calmodulin dependent protein kinase II (Hamon et al) and an activator protein I4-3-3 (Ichimura T. et al). However the calcium dependent protein kinase seems much more effective in activating tryptophan hydroxylase than human caudate tyrosine hydroxylase (Rausch W. D. et al). Ferrous iron or calcium activate tryptophan hydroxylase but copper does not (Imai Y. et al) whereas calcium calmodulin only barely increases tyrosine hydroxylase activity (Rausch et al). Dopamine beta hydroxylase is specifically copper dependent, four imidazole ligands binding to copper was demonstrated by pulsed electron paramagnetic resonance (McCracken J. et al). Both coppers in the subunit undergo reduction and reoxidation with formation of a copper hydroxyperoxide intermediate during catalysis (Klinman J. P.). The differing redox effects reported previously by Barbeau and Ekstrom for MPTP and its free radical products MPDP+ and MPP+ result from mobilization of copper and sequestering of iron at various subcellular sites.

Interactions of organic radicals with metals

The expected behavior of TEMPO in oxidizing reduced metals would be to diminish iron and copper dependent enzymatic activities as indeed was observed in the reduced levels of dopamine, norepinephrine and serotonin. Interestingly, PBN had similar effects to TEMPO, indicating overlapping chemical actions. TEMPO and PBN in combination with MPTP, antagonized the copper dependent effect on dopamine beta hydroxylase and were without effect in antagonizing MPTP-induced increase in tryptophan hydroxylase. The inability of TEMPO and PBN when co administered with MPTP to reduce serotonin likely relates to their lack of effect on free calcium which MPTP does influence. Due to the metal dependence of the reactions which generate these neuroamines, it seems likely that MPTP mobilizes copper and calcium, and sequesters iron. Given the similarities between MPTP and TEMPO and PBN actions it agrees with the in vitro conclusions that MPTP and MPP+ are reducing agents.

DEVELOPMENT PROGRAM

Therapeutic

Small animal and mammalian studies of polyamines compounds of the general formula below and derivatives thereof are in progress.

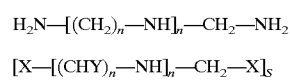

$$[X-[(CHY)_n-NH]_n-CH_2-X]_S$$

where the terminal amino groups may be substituted with X, and methylene groups substituted with Y and S when present makes a salt compound.

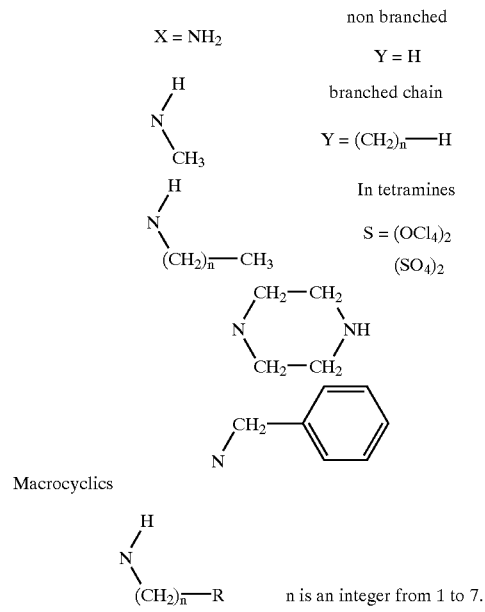

Macrocyclics

Branched aliphatic examples are more lipid soluble. Some of the linear and branched aliphatic examples inhibit ornithine decarboxylase, reducing endogenous polyamine synthesis and thus are not optimal compounds. Tetramine examples such as 2,3,2 tetramine are prepared as salts; $(OCl_4)_2$ and $(SO_4)_2$.

Comparison of actions of polyamines, 2,3,2 tetramine, 2,2,2 tetramine, 3,3,3 tetramine, cyclam, tet a as compounds therapy in animal models and subsequently clinical trials will be performed in Parkinson's Disease, Alzheimer's Disease, Guamanian Parkinsonian Dementia, Amyotrophic Lateral Sclerosis, Olivopontine Cerebellar Atrophy, Hereditary Cerebral Hemorrhage—Dutch Type and in Batten's Disease, Binswanger's Disease and Amyloid Angiopathy patients.

In 2,2,2 tetramine and 3,3,3 tetramine the CuN4 structure is distorted by contrast with the approximately planar structure of CuN4 in 2,3,2 tetramine, 1,4,8,11 tetra-azocyclotetradecane (cyclam) and meso-5,7,7,12,14,14-hexamethyl-1,4,8,11 tetra-azocyclotetradecane (tet a or meso-1,7 CTH), 1,4,7,10 tetrazocyclotetradecane, 1,4,7,10 tetraazocyclotridecane, 1,4,7-triazacyclononane, 3 azapentane-1,5-diamine. Comparisons of planarity and other conformational details are used to understand the effectiveness of various linear, branched and cyclic polyamines as copper removing agents, as metal translocating agents between storage sites and review of their effects on metallothionein induction, protein kinase C inhibition, NMDA receptor actions and limitation of DNA damage.

The following are examples of linear, branched and cyclic polyamines for comparative studies.

Non cyclic tetramines include;
  3,3'3" triaminotripropylamine (tpt),
  N,N'-di(3-aminopropyl)propylenediamine (3,3,3 -tet)
  2,2',2"-triaminotriethylamine (tren)
  N,N'-di(2-aminoethyl)ethylenediamine (trien)
  N,N'-di(2-aminoethyl)propylenediamine (2,3,2-tet)
Cyclic tetramines include derivatives of;
  1,4,8,11 tetra-azocyclotetradecane (cyclam)
    meso-5,7,7,12,14,14-hexamethyl-1,4,8,11 tetra-azocyclotetradecane (tet a or meso-1,7 CTH), 1,4,7,10 tetra-azocyclotetradecane, 1,4,7,10 tetraazocyclotridecane, 1,4,7-triazacyclononane, 3 azapentane-1,5-diamine.

The polyethylene polyamines are of the general formula NH2(CH2CH2NH)nH where n is an integer between 1 and 5, including diethylene triamine, triethylene tetramine, tetraethylene pentamine, pentaethylene hexamine and hexaethylene heptamine, propanediamine, aminopropylethylenediamine, bisaminopropylethylenediamine, hexamethylenediamine, mono or diethanolamine, and aminoethylethanolamine.

Cyclic polyethylene polyamines include propylene linked;
  triethylenetetramine-tetraethylene pentamine,
  aminoethylpiperazine,
  diethylenetriamine-triethylenetetramine
  tetraethylenepentamine
  aminoethylpiperazine-triethylenetetriamine
  aminoethylpiperazine-tetraethylenepentamine
  diethylenetriamine-amino-propylated triethylenetetramine
  triethylenetetramine
  diethylenetriamine
Investigation of other compound families in dementias in relation to similar and contrasting biochemical activities is also relevant;
  imidazole polycyclic iminoisoindoline chelates, alkylaminoesters of phosphoric acid, alpha amino acid diamides, hydroxamic acids, N carboxymethyl-N-(hydroxybenzyl)-asparagic acids, N,N fluorinated bisacyl hydrazides and tetrakisacylhydrazides, and branched compounds of the above families.

Diagnostic Tests

Assay of mitochondrial DNA damage in Parkinson's disease and Alzheimer's disease using leucocytes and urine.

Assay of endogenous polyamines in Parkinson's disease and Alzheimer's disease and Pick's disease using urine and cerebrospinal fluid.

Assay of Enkephalin and Cytocrophin peptides in cerebrospinal fluid of Parkinson's disease and Alzheimer's disease patients.

Conclusion

Thus, 2,3,2 Tetramine and similarly behaving compounds can provide a sequential methodology to the diagnosis and treatment of Parkinson's Disease, Alzheimer's Disease, Guamanian Parkinsonian Dementia, Amyotrophic Lateral Sclerosis, Olivopontine Cerebellar Atrophy, Hereditary Cerebral Hemorrhage—Dutch Type, Batten's Disease, neuronal component of Binswanger's Disease and Amyloid Angiopathy. An understanding is derived of why particular neurons are primary targets in these diseases, a mechanism of progression from Parkinson's Disease to Alzheimer's Disease and how differing etiologic events determine the patterns of damage in Parkinson's Disease and Alzheimer's Disease versus the more downstream causes in Amyotrophic Lateral Sclerosis, Guamanian Parkinsonian Dementia, Olivopontine Cerebellar Atrophy, and at which steps diagnostic tests and therapy can be employed.

More specifically, these compounds provide multiple actions on a cascade of events extending from DNA damage to amyloid production;
  a) Competitive inhibition of uptake of xenobiotics at the polyamine transport site, such organic molecules being a cause of DNA damage;
  b) Limitation of mitochondrial DNA damage by removal of free copper, iron and nickel ions by the presence of an aliphatic tetramine;
  c) Induction of nerve growth factor, brain derived neuronotrophic factor and neuronotrophin-3 gene transcription;
  d) Regulation of affinity of NMDA receptors and blockade of the MK801 ion channel;
  e) Binding and conservation of reduced glutathione;
  f) Maintenance of the homeostasis of the redox environment in brain;
  g) Induction of metallothionein;
  h) Inhibition of protein kinase C;
  i) Non toxic chelation of divalent metals in brain;
  j) Regulation of activity of pre-aspartate proteases;
  k) Inhibition of superoxide dismutase, amine oxidase, monoamine oxidase B;
  l) Regulation of brain polyamine levels in dementias with maintenance of endogenous polyamine levels;

What is claimed is:

1. A method of treating Parkinson's, Alzheimer's, Lou Gehrig's, Binswanger's Diseases and, Olivopontine Cerebellar Atrophy in animals through steric protection of DNA, enhancement of transcription of growth factors sequences, regulation of the NMDA receptor and the activity of the MK801 ion channel and other brain cell physiological stabilizing phenomena, said method comprising administering to said animals an effective dose of polyamine taken from a group consisting of cyclic and linear and branched polyamines.

2. The method of claim 1, wherein said polyamines are taken from a group consisting of 2,3,2 tetramine, 2,2,2 tetramine and 3,3,3 tetramine.

3. The method of claim 2, wherein said animal is a Rana pipiens.

4. The method of claim 1, wherein symptoms of said diseases are induced by injecting said animal intraperitoneally with a single 40 mg/Kg dose of MPTP.

5. The method of claim 4, wherein said effective amount comprises a single 1.2 mM dose.

6. The method of claim 1, wherein said dose comprises 2,3,2 tetramine.

7. The method of claim 6, wherein said animal is a Rana pipiens.

8. The method of claim 7, wherein symptoms of said diseases are induced by injecting said animal intraperitoneally with a single 40 mg/Kg dose of MPTP.

9. The method of claim 8, wherein said effective amount comprises a single 1.2 mM dose.

10. The method of claim 1, wherein said polyamine has the general formula

where X is a terminal amino group; and wherein n is an integer from 1 to 7.

11. The method of claim 10, wherein said terminal amino group is taken from a group consisting of elements having the formulae:

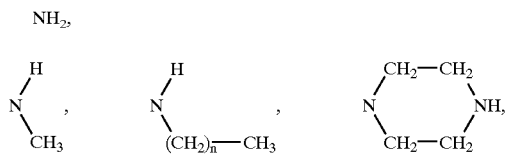

-continued

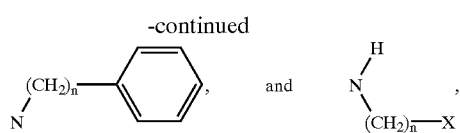

wherein n is an integer from 1 to 7.

12. The method of claim 1, wherein said polyamine has the general formula

wherein X is a terminal amino group, and Y is a methylene group; and wherein n is an integer from 1 to 7.

13. The method of claim 12, wherein said methylene group is

14. The method of claim 10, wherein said general formula further comprises a salt taken from a group consisting of $(OCl_4)_2$ and $(SO_4)_2$.

* * * * *